(12) United States Patent
He et al.

(10) Patent No.: US 11,148,302 B2
(45) Date of Patent: Oct. 19, 2021

(54) REMOTE-CENTER-OF-MOTION MECHANISM

(71) Applicant: Shanghai Microport Medbot (Group) Co., Ltd., Shanghai (CN)

(72) Inventors: Chao He, Shanghai (CN); Shuai Yuan, Shanghai (CN); Tingping Dai, Shanghai (CN)

(73) Assignee: SHANGHAI MICROPORT MEDBOT (GROUP) CO., LTD., Shanghai (CN)

(*) Notice: Subject to any disclaimer, the term of this patent is extended or adjusted under 35 U.S.C. 154(b) by 350 days.

(21) Appl. No.: 16/470,157

(22) PCT Filed: Dec. 18, 2017

(86) PCT No.: PCT/CN2017/116826
§ 371 (c)(1),
(2) Date: Jun. 14, 2019

(87) PCT Pub. No.: WO2018/108184
PCT Pub. Date: Jun. 21, 2018

(65) Prior Publication Data
US 2020/0009748 A1    Jan. 9, 2020

(30) Foreign Application Priority Data
Dec. 16, 2016    (CN) .......................... 201611169116.3

(51) Int. Cl.
*B25J 18/00*    (2006.01)
*B25J 5/00*    (2006.01)
(Continued)

(52) U.S. Cl.
CPC ............. *B25J 18/007* (2013.01); *B25J 5/007* (2013.01); *B25J 9/1065* (2013.01); *B25J 17/0266* (2013.01)

(58) Field of Classification Search
CPC ........ B25J 18/007; B25J 5/007; B25J 9/1065; B25J 17/0266
See application file for complete search history.

(56) References Cited

U.S. PATENT DOCUMENTS

| 4,451,196 A | * | 5/1984 | Harada | ................... B25J 9/1065 198/468.4 |
| 6,715,981 B1 | * | 4/2004 | Harsch | ................... B21D 43/05 414/752.1 |

(Continued)

FOREIGN PATENT DOCUMENTS

| CN | 101919739 A | 12/2010 |
| CN | 105287003 A | 2/2016 |

(Continued)

OTHER PUBLICATIONS

Aksungur et al; "Remote Center of Motion"; IJAMEC; 2015 (3)2; pp. 119-126.

*Primary Examiner* — Zakaria Elahmadi
(74) *Attorney, Agent, or Firm* — Muncy, Geissler, Olds & Lowe, P.C.

(57) ABSTRACT

Provided is a fixed point mechanism. In the fixed point mechanism, when a drive torque acts on a first connecting rod member (100) or a slide block device (110), the fixed point mechanism can realize a rotation movement around a fixed point; when a drive torque acts on a fourth connecting rod member (103) or a sixth connecting rod member (105), the fixed point mechanism can realize a telescopic movement relative to the fixed point; and when a drive torque acts on the first connecting rod member (100) or the slide block device (110), and another drive torque acts on the fourth connecting rod member (103) or the sixth connecting rod member (105), the fixed point mechanism can realize a rotation movement around the fixed point and a telescopic movement relative to the fixed point. That is, the fixed point (Continued)

mechanism has two degrees of freedom of the rotation movement around the fixed point and the telescopic movement relative to the fixed point.

13 Claims, 10 Drawing Sheets

(51) Int. Cl.
    *B25J 9/10* (2006.01)
    *B25J 17/02* (2006.01)

(56) References Cited

U.S. PATENT DOCUMENTS

| | | |
|---|---|---|
| 7,021,173 B2 | 4/2006 | Stoianovici et al. |
| 2006/0207377 A1* | 9/2006 | Gosselin .............. B25J 13/04 74/490.01 |
| 2007/0089557 A1* | 4/2007 | Solomon .............. A61B 34/37 74/490.01 |
| 2008/0014071 A1* | 1/2008 | McCaffrey .............. B66C 15/00 414/787 |
| 2013/0239735 A1 | 9/2013 | Solomon et al. |
| 2014/0248110 A1* | 9/2014 | Kfoury .............. B66C 23/005 414/680 |
| 2014/0276953 A1* | 9/2014 | Swarup .............. B25J 18/007 606/130 |
| 2015/0351857 A1* | 12/2015 | Vander Poorten ..... B25J 18/007 606/130 |
| 2019/0053863 A1* | 2/2019 | Hongo .............. B25J 9/06 |
| 2019/0209264 A1* | 7/2019 | Seo .............. B25J 9/1065 |

FOREIGN PATENT DOCUMENTS

| | | |
|---|---|---|
| CN | 105748153 A | 7/2016 |
| CN | 105852974 A | 8/2016 |
| CN | 106037936 A | 10/2016 |
| CN | 106584445 A | 4/2017 |
| DE | 10 2012 220 666 A1 | 5/2014 |
| EP | 0 595 291 A1 | 5/1994 |
| EP | 2736680 A | 6/2014 |
| WO | WO 2014/108545 A1 | 7/2014 |

\* cited by examiner

REMOTE-CENTER-OF-MOTION MECHANISM

TECHNICAL FIELD

The present application relates to the field of machinery and, particularly, to remote-center-of-motion mechanisms, more particularly, to a remote-center-of-motion mechanism with two degrees of freedom and suitable for use in the field of minimally invasive surgical robotics, especially in the field of robotic manipulator of surgical robotics.

BACKGROUND

Minimally invasive surgery refers to a new technique of surgical treatment carried out in vivo with endoscopes such as laparoscopes and thoracoscopes. It provides a range of advantages such as minimal wound, slight pain and less bleeding, which can effectively reduce patient's recovery time and discomfort and avoid side effects of traditional open surgery. Early minimally invasive surgery has the defects that the operation with surgical tools by doctor is relatively constrained due to the limitation of pores at body surface, and the operation direction may also be opposite to the desired direction, which increases the difficulty for the doctor to carry out surgery. As a result, the doctor can carry out the minimal invasive surgery smoothly only after a long-term relevant training.

With the development of science and technology, especially robotics technology, a better solution has been found to the problems in the early minimally invasive surgery, and thus the minimally invasive surgical robotic system has been researched and developed. The minimally invasive surgical robotic system enables the doctor to observe the characteristics of the tissue in vivo through a two-dimensional or three-dimensional display device at the surgeon's control console, and remotely manipulate manipulators and surgical instruments on the patient side cart to operate the surgery. It makes that the doctor operates the minimally invasive surgery with the feeling as the traditional open surgery. Meanwhile, it reduces the difficulty of the doctor in the operation, improves the efficiency and safety of the surgery, and makes a breakthrough in the realization of remote surgery. In view of the superiority of the surgical robotic system, countries in the world are actively doing research in related fields and have produced some products and prototypes.

As to surgical robotics, one of the critical issues to be urgently solved is that, during the movement of the manipulators of a patient-side of the robot, the surgical instrument mounted on the manipulators of the patient-side of the robot is kept moving around a small incision on the patient's body. In other words, the manipulator of the patient-side robot should comprise a remote-center-of-motion mechanism.

Remote-center-of-motion mechanisms have been the focus of researches in surgical robotics for long. The basic principle model of existing remote-center-of-motion mechanisms is substantially the double parallelogram principle allowing construct two parallelograms coupled to each other via connecting rod members and thus forming a remote center of motion at a specific position. For example, the remote-center-of-motion mechanisms described in Chinese Application No. CN101919739A and No. CN102813553A are both constructed using such principle. However, the double parallelogram itself has only one degree of freedom, i.e. the remote-center-of-motion mechanism based on the double parallelogram can pitch about the remote center of motion. In order to meet operation needs, the minimally invasive surgical robot further requires a degree of freedom in the plane of the structure, i.e. the telescopic degree of freedom. For the remote-center-of-motion mechanism based on double parallelogram, in order to achieve the telescopic degree of freedom, it requires the addition of components needed for the telescopic degree of freedom, thereby increasing the volume of the whole manipulator and its design complexity. Moreover, in the case where a plurality of manipulators are used in collaboration, the spatial position of each manipulator should be taken into consideration, which in turn imposing additional limitations on the robot and raising the complexity and difficulty of surgeon's operation.

SUMMARY

It is an object of the some of the embodiments to solve the problem that the remote center of motion formed by the conventional double parallelogram remote-center-of-motion mechanism has only one degree of freedom.

To solve the above problem, some embodiments provide a remote-center-of-motion mechanism, comprising active components, driven components and transmission components, wherein:

the active components comprise a first connecting rod member, a second connecting rod member, a third connecting rod member, a fourth connecting rod member and a slide block device, the first connecting rod member having a first end rotatably connected to a first end of the second connecting rod member via a first rotating shaft, the second connecting rod member having a second end rotatably connected to the slide block device via a second rotating shaft, the third connecting rod member being slidably connected to the slide block device, the third connecting rod member passing through an axis of the second rotating shaft, the third connecting rod member having a second end rotatably connected to a second end of the fourth connecting rod member via a third rotating shaft, the fourth connecting rod member having a first end rotatably connected to the first connecting rod member via a fourth rotating shaft;

the driven components comprise a fifth connecting rod member, a sixth connecting rod member and a seventh connecting rod member connected in sequence, the fifth connecting rod member having a first end rotatably connected to the fourth connecting rod member via a fifth rotating shaft, the fifth connecting rod member having a second end rotatably connected to the sixth connecting rod member via a sixth rotating shaft, the sixth connecting rod member having a second end rotatably connected to a second end of the seventh connecting rod member via a seventh rotating shaft, the sixth connecting rod member having a first end rotatably connected to a second end of the first connecting rod member via an eighth rotating shaft;

the transmission components comprise a first runner, a second runner, a third runner, a fourth runner and a flexible element, wherein:

the first runner and the third connecting rod member rotate about the third rotating shaft synchronously, the fourth runner and the seventh connecting rod member rotate about the seventh rotating shaft synchronously, and the first runner equals to the fourth runner in diameter, wherein the second runner is sleeved over the fifth rotating shaft, the third runner is sleeved over the sixth rotating shaft, the second runner equals to the third runner in diameter, the flexible element is fixedly connected to each of the first runner and the fourth runner and is wound around and passes the second runner and the third runner through sides of the second runner and the third runner away from the seventh connecting rod member, to form a closed transmission loop;

or wherein the first runner and the third connecting rod member rotate about the third rotating shaft synchronously, the fourth runner and the seventh connecting rod member rotate about the seventh rotating shaft synchronously, and the first runner equals to the fourth runner in diameter, and wherein the second runner is sleeved over the fourth rotating shaft, the third runner is sleeved over the eighth rotating shaft, the second runner equals to the third runner in diameter, the flexible element is fixedly connected to each of the first runner and the fourth runner and is wound around and passes the second runner and the third runner through sides of the second runner and the third runner away from the seventh connecting rod member, to form a closed transmission loop;

wherein a parallelogram can be formed by connecting virtual lines between an axis of the fourth rotating shaft, an axis of the fifth rotating shaft, an axis of the sixth rotating shaft and an axis of the eighth rotating shaft;

wherein each of the third connecting rod member and the seventh connecting rod members is a straight bar;

wherein a distance between an axis of the first rotating shaft and the axis of the fourth rotating shaft is in a first ratio to a distance between the axis of the first rotating shaft and the axis of the eighth rotating shaft, and a distance between an axis of the third rotating shaft and the axis of the fourth rotating shaft is in a second ratio to a distance between the axis of the eighth rotating shaft and an axis of the seventh rotating shaft, wherein the first ratio and the second ratio are configured to be equal; and wherein a first connecting line is formed by a virtual connecting line between the axis of the fifth rotating shaft and the axis of the fourth rotating shaft, a second connecting line is formed by a virtual connecting line between the axis of the fourth rotating shaft and the axis of the third rotating shaft, and a first angle is formed by the first connecting line and the second connecting line; wherein a third connecting line is formed by a virtual connecting line between the axis of the second rotating shaft and the axis of the third rotating shaft, and a second angle is formed by the third connecting line and the seventh connecting rod member; wherein a fourth connecting line is formed by a virtual connecting line between the axis of the first rotating shaft and the axis of the fourth rotating shaft, a fifth connecting line is formed by a virtual connecting line between the axis of the first rotating shaft and the axis of the eighth rotating shaft, and a third angle is formed by the fourth connecting line and the fifth connecting line; wherein the first angle, the second angle and the third angle are configured to be equal.

Optionally, in the remote-center-of-motion mechanism, the first angle may range from −30° to 30°.

Optionally, in the remote-center-of-motion mechanism, the first angle may be 0°, −15° or 15°.

Optionally, in the remote-center-of-motion mechanism, the first ratio may range from 1/12 to 1/2.

Optionally, in the remote-center-of-motion mechanism, each of the second runner and the third runner may be a single wheel or each of the second runner and the third runner may be implemented as a set of single wheels.

The other embodiments provide another remote-center-of-motion mechanism comprising active components, driven components and transmission components, wherein:

the active components comprise a first connecting rod member, a second connecting rod member, a third connecting rod member, a fourth connecting rod member and a slide block device, the first connecting rod member having a first end rotatably connected to a first end of the second connecting rod member via a first rotating shaft, the second connecting rod member having a second end rotatably connected to the slide block device via a second rotating shaft, the third connecting rod member being slidably connected to the slide block device, the third connecting rod member passing through an axis of the second rotating shaft, the third connecting rod member having a second end rotatably connected to a second end of the fourth connecting rod member via a third rotating shaft, the fourth connecting rod member having a first end rotatably connected to the first connecting rod member via a fourth rotating shaft;

the driven components comprise a fifth connecting rod member, a sixth connecting rod member and a seventh connecting rod member connected in sequence, the fifth connecting rod member having a first end rotatably connected to the fourth connecting rod member via a fifth rotating shaft, the fifth connecting rod member having a second end rotatably connected to the sixth connecting rod member via a sixth rotating shaft, the sixth connecting rod member having a second end rotatably connected to a second end of the seventh connecting rod member via a seventh rotating shaft, the sixth connecting rod member having a first end rotatably connected to a second end of the first connecting rod member via an eighth rotating shaft;

the transmission components comprise a first runner, a second runner, a third runner, a fourth runner and a flexible element, wherein:

the first runner and the third connecting rod member rotate about the third rotating shaft synchronously, the fourth runner and the seventh connecting rod member rotate about the seventh rotating shaft synchronously, the first runner equals to the fourth runner in diameter, the second runner is sleeved over the fifth rotating shaft, the third runner is sleeved over the sixth rotating shaft, the second runner equals to the third runner in diameter, the flexible element is fixedly connected to each of the first runner and the fourth runner and is wound around and passes the second runner and the third runner through sides of the second runner and the third runner away from the seventh connecting rod member, to form a closed transmission loop;

or wherein the first runner and the third connecting rod member rotate about the third rotating shaft synchronously, the fourth runner and the seventh connecting rod member rotate about the seventh rotating shaft synchronously, the first runner equals to the fourth runner in diameter, and wherein the second runner is sleeved over the fourth rotating shaft, the third runner is sleeved over the eighth rotating shaft, the second runner equals to the third runner in diameter, the flexible element is fixedly connected to each of the first runner and the fourth runner and is wound around and passes the second runner and the third runner through sides of the second runner and the third runner away from the seventh connecting rod member, to form a closed transmission loop;

wherein a parallelogram can be formed by connecting virtual lines between an axis of the fourth rotating shaft, an axis of the fifth rotating shaft, an axis of the sixth rotating shaft and an axis of the eighth rotating shaft;

wherein the third connecting rod member comprises a fifth connecting rod member section connected to the third rotating shaft and a sixth connecting rod member section slidably connected to the slide block device, the sixth connecting rod member section is a straight bar, the fifth connecting rod member section is fixedly connected to the sixth connecting rod member section, and a distance from the third rotating shaft to the sixth connecting rod member section defines a first segment; wherein the seventh connecting rod member comprises a seventh connecting rod member section connected to the seventh rotating shaft and an eighth connecting rod member section, the eighth connecting rod member section is a straight bar, the seventh connecting rod member section is fixedly connected to the eighth connecting rod member section, and a distance from the seventh rotating shaft to the eighth connecting rod member section defines a second segment;

wherein a distance between an axis of the first rotating shaft and the axis of the fourth rotating shaft is in a first ratio to a distance between the axis of the first rotating shaft and the axis of the eighth rotating shaft, a distance between an axis of the third rotating shaft and the axis of the fourth rotating shaft is in a second ratio to a distance between the axis of the eighth rotating shaft and an axis of seventh rotating shaft, the first segment is in a third ratio to the second segment, and the first ratio, the second ratio and the third ratio are configured to be equal; and wherein a first connecting line is formed by a virtual connecting line between the axis of the fifth rotating shaft and the axis of the fourth rotating shaft, a second connecting line is formed by a virtual connecting line between the axis of the fourth rotating shaft and the axis of the third rotating shaft, a first angle is formed by the first connecting line and the second connecting line and a second angle is formed between the third connecting rod member and the seventh connecting rod member; wherein a fourth connecting line is formed by a virtual connecting line between the axis of the first rotating shaft and the axis of the fourth rotating shaft, a fifth connecting line is formed by a virtual connecting line between the axis of the first rotating shaft and the axis of the eighth rotating shaft, and a third angle is formed by the fourth connecting line and the fifth connecting line; wherein the first angle, the second angle and the third angle are configured to be equal.

Optionally, in the remote-center-of-motion mechanism, the first angle may range from −30° to 30°.

Optionally, in the remote-center-of-motion mechanism, the first angle may be 0°, −15° or 15°.

Optionally, in the remote-center-of-motion mechanism, the first ratio may range from 1/12 to 1/2.

Optionally, in the remote-center-of-motion mechanism, the fifth connecting rod member section is a straight bar with a fourth angle being formed by the fifth connecting rod member section and the sixth connecting rod member section, and the seventh connecting rod member section is also a straight bar with a fifth angle being formed by the seventh connecting rod member section and the eighth connecting rod member section, wherein the fifth angle is configured to be equal to the fourth angle.

Optionally, the fourth angle may range from 0° to 180°.

The other embodiments further provide another remote-center-of-motion mechanism comprising active components, driven components and transmission components, wherein:

the active components comprise a first connecting rod member, a second connecting rod member, a third connecting rod member, a fourth connecting rod member and a slide block device, the first connecting rod member having a first end rotatably connected to a first end of the second connecting rod member via a first rotating shaft, the second connecting rod member having a second end rotatably connected to the third connecting rod member via a second rotating shaft, the fourth connecting rod member having a second end rotatably connected to the slide block device via a third rotating shaft, the third connecting rod member being slidably connected to the slide block device, the third connecting rod member passing through an axis of the third rotating shaft, the fourth connecting rod member having a first end rotatably connected to the first connecting rod member via a fourth rotating shaft;

the driven components comprise a fifth connecting rod member, a sixth connecting rod member and a seventh connecting rod member connected in sequence, the fifth connecting rod member having a first end rotatably connected to the fourth connecting rod member via a fifth rotating shaft, the fifth connecting rod member having a second end rotatably connected to the sixth connecting rod member via a sixth rotating shaft, the sixth connecting rod member having a second end rotatably connected to a second end of the seventh connecting rod member via a seventh rotating shaft, the sixth connecting rod member having a first end rotatably connected to a second end of the first connecting rod member via an eighth rotating shaft;

the transmission components comprise a first runner, a second runner, a third runner, a fourth runner and a flexible element, wherein:

the first runner and the third connecting rod member rotate about the third rotating shaft synchronously, the fourth runner and the seventh connecting rod member rotate about the seventh rotating shaft synchronously, the first runner equals to the fourth runner in diameter, wherein the second runner is sleeved over the fifth rotating shaft, the third runner is sleeved over the sixth rotating shaft, the second runner equals to the third runner in diameter, the flexible element is fixedly connected to each of the first runner and the fourth runner and is wound around and passes the second runner and the third runner through sides of the second runner and the third runner away from the seventh connecting rod member, to form a closed transmission loop;

or wherein the first runner and the third connecting rod member rotate about the third rotating shaft synchronously, the fourth runner and the seventh connecting rod member rotate about the seventh rotating shaft synchronously, the first runner equals to the fourth runner in diameter, and wherein the second runner is sleeved over the fourth rotating shaft, the third runner is sleeved over the eighth rotating shaft, the second runner equals to the third runner in diameter, the flexible element is fixedly connected to each of the first runner and the fourth runner and is wound around and passes the second runner and the third runner through sides of the second runner and the third runner away from the seventh connecting rod member, to form a closed transmission loop;

wherein a parallelogram can be formed by connecting virtual lines between an axis of the fourth rotating shaft, an axis of the fifth rotating shaft, an axis of the sixth rotating shaft and an axis of the eighth rotating shaft;

wherein each of the third connecting rod member and the seventh connecting rod members is a straight bar;

wherein a distance between an axis of the first rotating shaft and the axis of the fourth rotating shaft is in a first ratio to a distance between the axis of the first rotating shaft and the axis of the eighth rotating shaft, and a distance between the axis of the third rotating shaft and the axis of the fourth rotating shaft is in a second ratio to a distance between the axis of the eighth rotating shaft and an axis of the seventh rotating shaft, wherein the first ratio is configured to be equal to the second ratio; and wherein a first connecting line is formed by a virtual connecting line between the axis of the fifth rotating shaft and the axis of the fourth rotating shaft, a second connecting line is formed by a virtual connecting line between the axis of the fourth rotating shaft and the axis of the third rotating shaft, and a first angle is formed by the first connecting line and the second connecting line; wherein a third connecting line is formed by a virtual connecting line between an axis of the second rotating shaft and the axis of third rotating shaft, and a second angle is formed by the third connecting line and the seventh connecting rod member; wherein a fourth connecting line is formed by a virtual connecting line between the axis of the first rotating shaft and the axis of the fourth rotating shaft, a fifth connecting line is formed by a virtual connecting line between the axis of the first rotating shaft and the axis of the eighth rotating shaft, and a third angle is formed by the fourth connecting line and the fifth connecting line; wherein the first angle, the second angle and the third angle are configured to be equal.

The other embodiments yet further provide another remote-center-of-motion mechanism comprising active components, driven components and transmission components, wherein: the active components comprise a first connecting rod member, a second connecting rod member, a third connecting rod member, a fourth connecting rod member and a slide block device, the first connecting rod member having a first end rotatably connected to a first end of the second connecting rod member via a first rotating shaft, the second connecting rod member having a second end rotatably connected to the third connecting rod member via a second rotating shaft, the fourth connecting rod member having a second end rotatably connected to the slide block device via a third rotating shaft, the third connecting rod member being slidably connected to the slide block device and not passing through an axis of the third rotating shaft, the fourth connecting rod member having a first end rotatably connected to the first connecting rod member via a fourth rotating shaft;

the driven components comprise a fifth connecting rod member, a sixth connecting rod member and a seventh connecting rod member connected in sequence, the fifth connecting rod member having a first end rotatably connected to the fourth connecting rod member via a fifth rotating shaft, the fifth connecting rod member having a second end rotatably connected to the sixth connecting rod member via a sixth rotating shaft, the sixth connecting rod member having a second end rotatably connected to a second end of the seventh connecting rod member via a seventh rotating shaft, the sixth connecting rod member having a first end rotatably connected to a second end of the first connecting rod member via an eighth rotating shaft;

the transmission components comprise a first runner, a second runner, a third runner, a fourth runner and a flexible element, wherein:

the first runner and the third connecting rod member rotate about the third rotating shaft synchronously, the fourth runner and the seventh connecting rod member rotate about the seventh rotating shaft synchronously, and the first runner equals to the fourth runner in diameter, and wherein the second runner is sleeved over the fifth rotating shaft, the third runner is sleeved over the sixth rotating shaft, the second runner equals to the third runner in diameter, the flexible element is fixedly connected to each of the first runner and the fourth runner and is wound around and passes the second runner and the third runner through sides of the second runner and the third runner away from the seventh connecting rod member, to form a closed transmission loop;

or wherein the first runner and the third connecting rod member rotate about the third rotating shaft synchronously, the fourth runner and the seventh connecting rod member rotate about the seventh rotating shaft synchronously, and the first runner equals to the fourth runner in diameter, and wherein the second runner is sleeved over the fourth rotating shaft, the third runner is sleeved over the eighth rotating shaft, the second runner equals to the third runner in diameter, the flexible element is fixedly connected to each of the first runner and the fourth runner and is wound around and passes the second runner and the third runner through sides of the second runner and the third runner away from the seventh connecting rod member, to form a closed transmission loop;

wherein a parallelogram can be formed by connecting virtual lines between an axis of the fourth rotating shaft, an axis of the fifth rotating shaft, an axis of the sixth rotating shaft and an axis of the eighth rotating shaft;

wherein the third connecting rod member is a straight bar, a distance from the third rotating shaft to the third connecting rod member defines a first segment; wherein the seventh connecting rod member comprises a seventh connecting rod member section connected to the seventh rotating shaft and an eighth connecting rod member section, and the seventh connecting rod member section is partially fixedly connected to the eighth connecting rod member section; wherein the eighth connecting rod member section is a straight bar, and a distance from the seventh rotating shaft to the eighth connecting rod member section defines a second segment;

wherein a distance between an axis of the first rotating shaft and the axis of the fourth rotating shaft is in a first ratio to a distance between the axis of the first rotating shaft and the axis of the eighth rotating shaft, a distance between an axis of the third rotating shaft and the axis of the fourth rotating shaft is in a second ratio to a distance between the axis of the eighth rotating shaft and an axis of the seventh rotating shaft, the first segment is in a third ratio to the second segment, and the first ratio, the second ratio and the third ratio are configured to be equal; and wherein a first connecting line is formed by a virtual connecting line between the axis of the fifth rotating shaft and the axis of the fourth rotating shaft, a second connecting line is formed by a virtual connecting line between the axis of the fourth rotating shaft and the axis of the third rotating shaft, a first angle is formed by the first connecting line and the second connecting line, and a second angle is formed by the third connecting rod member and the seventh connecting rod member, wherein a fourth connecting line is formed by a virtual connecting line between the axis of the first rotating shaft and the axis of the fourth rotating shaft, a fifth connecting line is formed by a virtual connecting line between the axis of the first rotating shaft and the axis of the eighth rotating shaft, a third angle is formed by the fourth connecting line and the fifth connecting line, and the first angle, the second angle and the third angle are configured to be equal.

In the application, the remote-center-of-motion mechanisms are able to rotate around the remote center of motion when a driving torque is acted on the first connecting rod member or the slide block device; the remote-center-of-motion mechanisms are able to achieve telescopic movement relative to the remote center of motion, when a driving torque is applied to the fourth connecting rod member or the sixth connecting rod member; and the remote-center-of-motion mechanisms are able to rotate around the remote center of motion as well as to make telescopic movement relative to the remote center of motion when one driving torque is acted on the first connecting rod member or the slide block device with another driving torque being exerted on the fourth connecting rod member or the sixth connecting rod member. That is, the remote-center-of-motion mechanisms have two degrees of freedom of the rotational movement around remote center of motion and the telescopic movement relative to remote center of motion.

IN FIGURES

First Connecting rod member: 100, 200, 300, 400, 500, 600, 700, 800
Second Connecting rod member: 101, 201, 301, 401, 501, 601, 701, 801
Third Connecting rod member: 102, 202, 302, 402, 502, 602, 702, 802
Fourth Connecting rod member: 103, 203, 303, 403, 503, 603, 703, 803
Fifth Connecting rod member: 104, 204, 304, 404, 504, 604, 704, 804
Sixth Connecting rod member: 105, 205, 305, 405, 505, 605, 705, 805
Seventh Connecting rod member: 106, 206, 306, 406, 506, 606, 706, 806
Slide block device: 110, 210, 310, 410, 510, 610, 710, 810
First Rotating shaft: 120, 220, 320, 420, 520, 620, 720, 820
Second Rotating shaft: 121, 221, 321, 421, 521, 621, 721, 821
Third Rotating shaft: 122, 222, 322, 422, 522, 622, 722, 822
Fourth Rotating shaft: 123, 223, 323, 423, 523, 623, 723, 823
Fifth Rotating shaft: 124, 224, 324, 424, 524, 624, 724, 824
Sixth Rotating shaft: 125, 225, 325, 425, 525, 625, 725, 825
Seventh Rotating shaft: 126, 226, 326, 426, 526, 626, 726, 826
Eighth Rotating shaft: 127, 227, 327, 427, 527, 627, 727, 827
First Runner: 130, 230, 330, 430, 530, 630, 730, 830
Second Runner: 131, 231, 331, 431, 531, 631, 731, 831
Third Runner: 132, 232, 332, 432, 532, 632, 732, 832
Fourth Runner: 133, 233, 333, 433, 533, 633, 733, 833
Flexible Element: S1, S2, S3, S4, S5, S6, S7, S8
Remote Center of Motion: D1, D2, D3, D4, D5, D6, D7, D8

DETAILED DESCRIPTION

The remote-center-of-motion mechanism provided in the present application will be described in more detail with reference to the accompanying drawings and specific embodiments. Advantages and features of the application will become more apparent from the following description and appended claims. It should be noted that the drawings are in a very simplified form and not necessarily presented to scale, for the only purpose to facilitate convenient and explicit description of embodiments of the present application. In particular, the drawings are shown in different scale for emphasizing different content.

For unity and clarity of the expression, in the terms of present application, a lower or proximal end of each of the illustrated connecting rod members (including first connecting rod member, the second connecting rod member, the third connecting rod member, the fourth connecting rod member, the fifth connecting rod member, the sixth connecting rod member and the seventh connecting rod member) is referred to as a first end, and an upper or distal end thereof is referred to as a second end.

Embodiment 1

Figure 1:
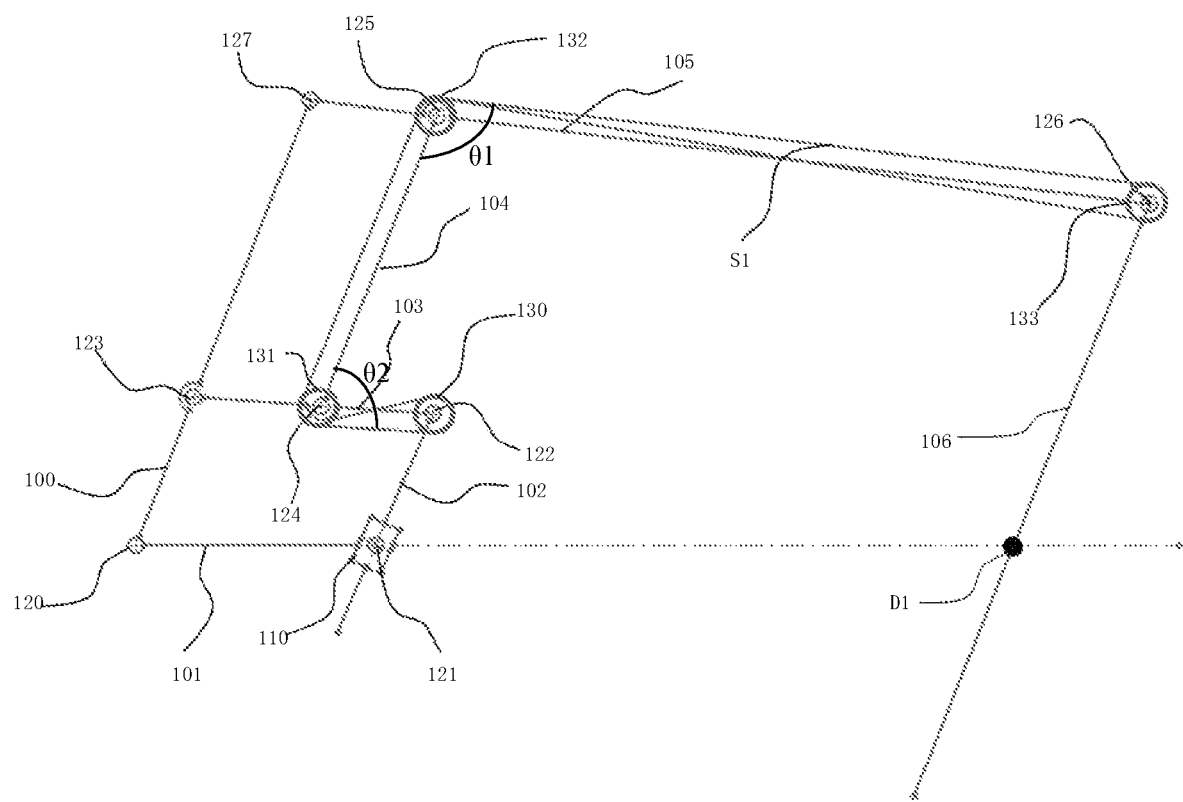
FIG. 1 is a schematic diagram illustrating the principle of a remote-center-of-motion mechanism according to Embodiment 1.

Reference is now made to FIG. 1, a schematic diagram illustrating the principle of a remote-center-of-motion mechanism according to Embodiment 1. As shown in FIG. 1, the remote-center-of-motion mechanism 1 includes active components, driven components and transmission components. Specifically, the active components include a first connecting rod member 100, a second connecting rod member 101, a third connecting rod member 102, a fourth connecting rod member 103 and a slide block device 110. A first (here, lower) end of the first connecting rod member 100 is rotatably connected to a first (here, proximal) end of the second connecting rod member 101 via a first rotating shaft 120. A second (here, distal) end of the second connecting rod member 101 is rotatably connected to the slide block device 110 via a second rotating shaft 121. The third connecting rod member 102 is slidably connected to the slide block device 110 and passes through the axis of the second rotating shaft 121. A second (here, upper) end of the third connecting rod member 102 is rotatably connected to a second (here, distal) end of the fourth connecting rod member 103 via a third rotating shaft 122. A first (here, proximal) end of the fourth connecting rod member 103 is rotatably connected to the first connecting rod member 100 via a fourth rotating shaft 123. Here, the term "slidably connected" means that the third connecting rod member 102 and the slide block device 110 constitute a slide block structure of guide rail, that is, the third connecting rod member 102 can only move along the direction constrained by the slide block device 110. The same applies hereinafter.

The driven components include a fifth connecting rod member 104, a sixth connecting rod member 105 and a seventh connecting rod member 106 connected in sequence. A first (here, lower) end of the fifth connecting rod member 104 is rotatably connected to the fourth connecting rod member 103 via a fifth rotating shaft 124, and a second (here, upper) end of the fifth connecting rod member 104 is rotatably connected to the sixth connecting rod member 105 via a sixth rotating shaft 125. A second (here, distal) end of the sixth connecting rod member 105 is rotatably connected to a second (here, upper) end of the seventh connecting rod member 106 via a seventh rotating shaft 126, and a first (here, proximal) end of the sixth connecting rod member 105 is rotatably connected to a second (here, upper) end of the first connecting rod member 100 via an eighth rotating shaft 127.

The transmission components include a first runner 130, a second runner 131, a third runner 132, a fourth runner 133 and a flexible element 51. The first runner 130 and the third connecting rod member 102 rotate about the third rotating shaft 122 synchronously. The second runner 131 is sleeved over the fifth rotating shaft 124, and the third runner 132 is sleeved over the sixth rotating shaft 125. The fourth runner 133 and the seventh connecting rod member 106 rotate about the seventh rotating shaft 126 synchronously. The flexible element 51 is fixedly connected to each of the first runner 130 and the fourth runner 133 and is wound around and passes the second runner 131 and the third runner 132 through sides of the second runner 131 and the third runner 132 away from the seventh connecting rod member 106, to form a closed transmission loop. The first runner 130 is equal to the fourth runner 133 in diameter, and the third runner 132 is equal to the second runner 131 in diameter. Here, the "fixed connection" between the flexible element 51 and a runner is intended to mean that the flexible element 51 is partially wound around the rim of the runner and sufficient friction is existed between flexible element 51 and the said runner such that there is no relative motion therebetween, i.e. there is no slippage. The same applies hereinafter.

The winding path of the flexible element 51 can form angles similar to complementary wrap angles of a parallelogram. That is, the flexible element 51 passes through the third runner 132 and the second runner 131 from sides of the third runner 132 and the second runner 131 away from the seventh connecting rod member 106, and forms a first wrap angle θ1 with the third runner 132 and a second wrap angle θ2 with the second runner 131. When a driving torque is acted on the first connecting rod member 100 or the slide block device 110, or when a driving torque is acted on the fourth connecting rod member 103 or the sixth connecting rod member 105, the change value of the first wrap angle θ1 equals to the change value of the second wrap angle θ2 in number.

In this Embodiment, a forward path and a return path of the flexible element 51 are formed at the same side of the third runner 132 and the second runner 131. That is, the forward path and the return path of the flexible element 51 shares a same set of runners, i.e., the third runner 132 and the second runner 131, which are equal in diameter. In other embodiments of the present application, the forward path and the return path of the flexible element 51 may also use respective sets of runners, i.e. each of the third runner 132 and the second runner 131 comprises two runners forming two sets of runners. That is, the third runner 132 shown in FIG. 1 is replaced with a third runner A and a third runner B, and the second runner 131 shown in FIG. 1 is replaced with a second runner A and a second runner B. The third runner A and the second runner A constitute one set of runners, and the third runner B and the second runner B constitute the other set of runners. The forward path of the flexible element 51 may be constrained along one side of the third runner A and the second runner A, while the return path of the flexible element 51 may be constrained along one side of the third runner B and the second runner B. The third runner A is equal to the second runner A in diameter, and the third runner B is equal to the second runner B in diameter. The diameter of third runner A and the third runner B may be equal or not. On the other hand, the second runner 131 may be fixedly or rotatably connected to the fifth rotating shaft 124, i.e. relative motion is allowed between the second runner 131 and the fifth rotating shaft 124. The third runner 132 is connected to the sixth rotating shaft 125 in a similar manner.

In this Embodiment, the first runner 130 may be fixedly connected to the third connecting rod member 102 so as to achieve synchronous rotation of the first runner 130 and the third connecting rod member 102 about the third rotating shaft 122. Alternatively, each of the first runner 130 and the third connecting rod member 102 may be fixedly connected to the third rotating shaft 122 so that the first runner 130 and the third connecting rod member 102 rotating about the third rotating shaft 122 synchronously is achieved.

A parallelogram can be formed by connecting virtual lines between the axis of the fourth rotating shaft 123, the axis of the fifth rotating shaft 124, the axis of the sixth rotating shaft 125 and the axis of the eighth rotating shaft 127.

The distance between the axis of the first rotating shaft 120 and the axis of the fourth rotating shaft 123 is in a first ratio to the distance between the axis of the first rotating shaft 120 and the axis of eighth rotating shaft 127, and the distance between the axis of the third rotating shaft 122 and the axis of the fourth rotating shaft 123 is in a second ratio to the distance between the axis of the eighth rotating shaft 127 and the axis of seventh rotating shaft 126. The first ratio is configured to be equal to the second ratio. Only when the first ratio is equal to the second ratio, can it be ensured that variation of the angle formed by the third connecting rod member 102 and the fourth connecting rod member 103 of the remote-center-of-motion mechanism 1 equals to the variation of angle formed by the sixth connecting rod member 105 and the seventh connecting rod member 106 of the remote-center-of-motion mechanism 1 during the movement. In embodiments, each of the first ratio and the second ratio preferably ranges from 1/12 to 1/2. In an exemplary Embodiment, each of the first and second ratios is 1/6.

The first connecting line is formed by the virtual connecting line between the axis of the fifth rotating shaft 124 and the axis of the fourth rotating shaft 123, and the second connecting line is formed by the virtual connecting line between the axis of the fourth rotating shaft 123 and the axis of the third rotating shaft 122. The first angle (having the first angular value) is formed by the first connecting line and the second connecting line. The third connecting line is formed by the virtual connecting line between the axis of the second rotating shaft 121 and the axis of the third rotating shaft 122. The second angle (having the second angular value) is formed by the third connecting line and the seventh connecting rod member 106. The fourth connecting line is formed by the virtual connecting line between the axis of the first rotating shaft 120 and the axis of the fourth rotating shaft 123, and the fifth connecting line is formed by the virtual connecting line between the axis of the first rotating shaft 120 and the axis of the eighth rotating shaft 127. The third angle (having a third angular value) is formed by the fourth connecting line and the fifth connecting line. The first angle, the second angle and the third angle are configured to be equal.

Further, according to the embodiments, the sign of the first angle, the second angle and the third angle is determined as follow: if the first connecting line coincides with the second connecting line after rotating counterclockwise about the axis of the fourth rotating shaft 123 by the first angular value, then the corresponding first angle is positive, and if the first connecting line coincides with the second connecting line after rotating clockwise about the axis of the fourth rotating shaft 123 by the first angular value, then the corresponding first angle is negative. Assuming that the first parallel line is a virtual straight line paralleling to the axial line of the seventh connecting rod member 106 and passing through the axis of the second rotating shaft 121, if the third connecting line coincides with the first parallel line after rotating clockwise or counterclockwise about the axis of the second rotating shaft 121 by the second angular value, then the corresponding second angle is positive or negative, respectively; and if the fourth connecting line coincides with the fifth connecting line after rotating clockwise or counterclockwise about the axis of the first rotating shaft 120 by the third angular value, then the corresponding third angle is positive or negative, respectively. According to the embodiment, a remote-center-of-motion mechanism can be achieved only when the first angle, the second angle and the third angle are not only equal in absolute value but also are both positive or negative. It will be appreciated by those skilled in the art that, if an angle of a mechanism has a negative angular value whereas its positive angular value equivalent of the said negative angular value (i.e., 360° minus the absolute value of the angular value of an angle) equals to the angular values of the other two angles, then the said mechanism falls into the protection scope of the embodiments. For example, in an exemplary embodiment, the first angle is −345°, the second angle and the third angles are both +15°. In this case, the three angles should be considered equal, and the technical solution of the said exemplary embodiment falls into the protection scope of the embodiments. Similarly, if an angle of a mechanism has a positive angular value whereas its negative angular value equivalent of the its positive angular value (i.e., the absolute value of the angular value of an angle minus 360°) equals to the angular values of the other two angles, then the said mechanism falls into the protection scope of the embodiments. The same applies hereinafter. For example, in an exemplary embodiment, the first angle may be +15°, the second angle and the third angle are both −345°. In this case, the three angles should be considered equal, and the technical solution of the said exemplary embodiment falls into the protection scope of the embodiments.

In embodiments, the first angle, the second angle and the third angle preferably range from −30° to 30°. In this Embodiment, the first angle, the second angle and the third angle are set to 0°. That is, the third rotating shaft 122, the fourth rotating shaft 123 and the fifth rotating shaft 124 are situated on a same straight virtual line, i.e. the fourth connecting rod member 103 is a straight bar and the first rotating shaft 120, the fourth rotating shaft 123 and the eighth rotating shaft 127 are also situated on a same straight virtual line, i.e. the first connecting rod member 100 is also a straight bar. Further, the third connecting rod member 102 is also a straight bar, and the seventh connecting rod member 106 is parallel to the third connecting rod member 102. That is, the seventh connecting rod member 106 is parallel to the virtual connecting line between the axis of the second rotating shaft 121 and the axis of the third rotating shaft 122.

In this Embodiment, the remote center of motion D1 is the intersection of the axial line of the seventh connecting rod member 106 and an imaginary extending line of the connecting line between the axis of the first rotating shaft 120 and the axis of the second rotating shaft 121. The first ratio or the second ratio is also equal to the ratio of the moving distance of the first (lower) end of the third connecting rod member 102 of the active components relative to the second rotating shaft 121 to the moving distance of the first (lower) end of the seventh connecting rod member 106 of the driven components relative to the remote center of motion D1 during the movement of the remote-center-of-motion mechanism 1.

Figure 2:
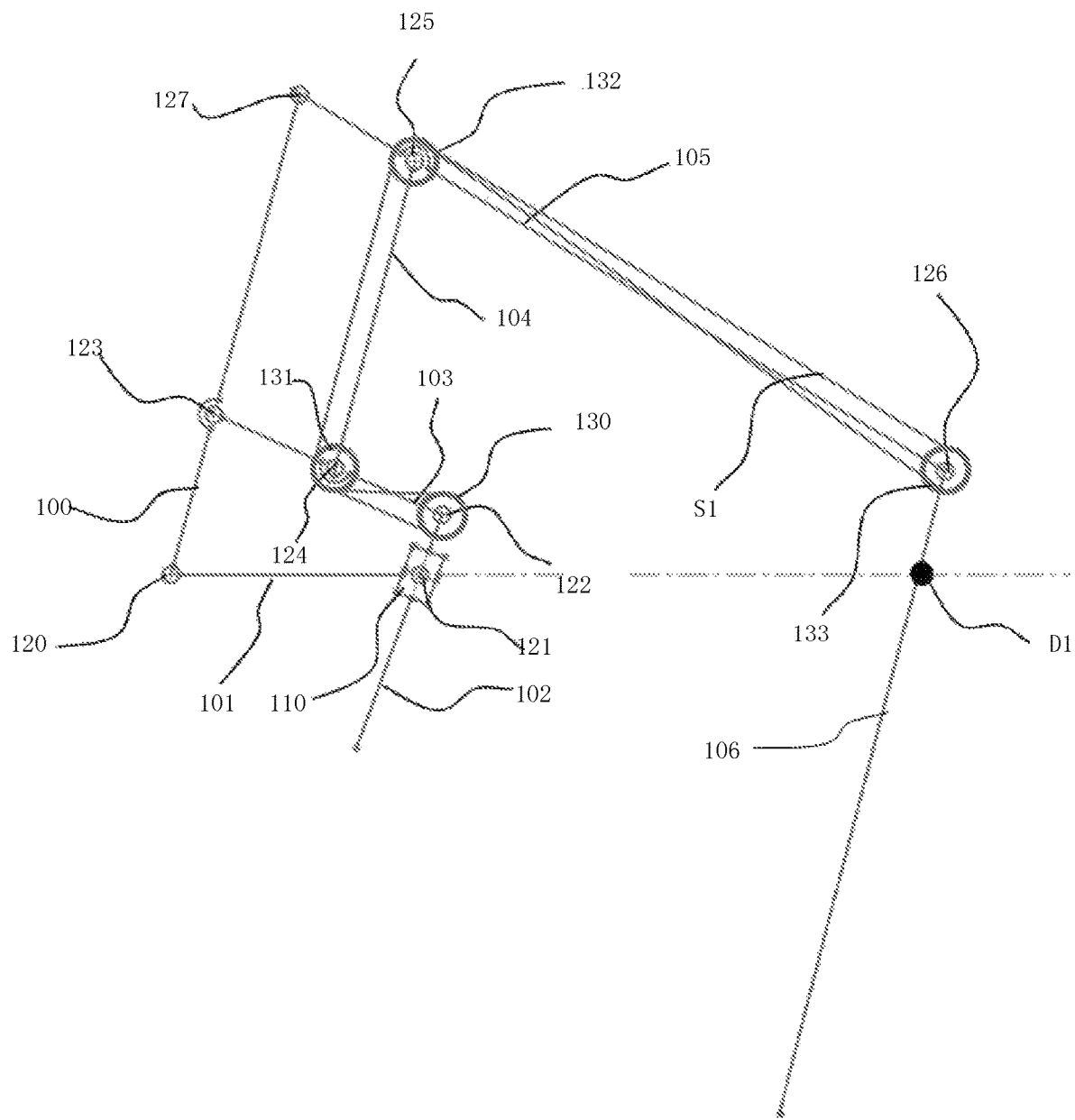
FIG. 2 is a schematic diagram illustrating the remote-center-of-motion mechanism of FIG. 1 after a movement.

Referring to FIGS. 1 and 2, taking the second connecting rod member 101 (whose imaginary extending line always passes through the remote center of motion D1) as a reference line, the remote-center-of-motion mechanisms 1 is able to rotate around the remote center of motion D1 when a driving torque is acted on the first connecting rod member 100 or the slide block device 110, which may be manifested, for example, as the change of the angle between the third connecting rod member 102 or the seventh connecting rod member 106 and the reference line; the remote-center-of-motion mechanism 1 is able to make telescopic movement relative to the remote center of motion D1 when a driving torque is exerted on the fourth connecting rod member 103 or the sixth connecting rod member 105, which may be manifested, for example, as the fourth connecting rod member 103 or the sixth connecting rod member 105 moving away from (extending) or toward (retracting) the remote center of motion D1. Further, the remote-center-of-motion mechanism 1 is able to rotate around the remote center of motion D1 as well as to make telescopic movement relative to the remote center of motion D1 when one driving torque is acted on the first connecting rod member 100 or the slide block device 110 and another driving torque is applied to the fourth connecting rod member 103 or the sixth connecting rod member 105. That is to say, the remote-center-of-motion mechanism 1 has two degrees of freedom of the rotational movement around remote center of motion D1 and the telescopic movement relative to remote center of motion D1.

Embodiment 2

Figure 3:
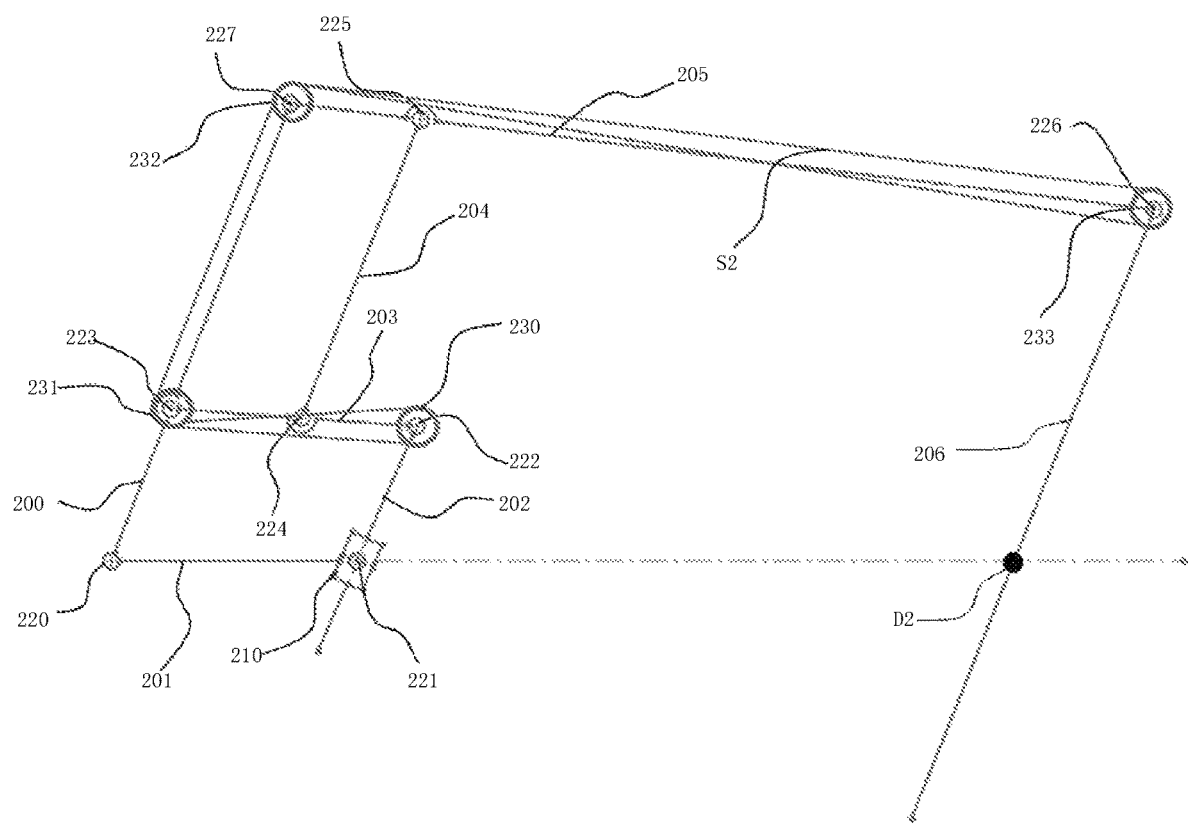
FIG. 3 is a schematic diagram illustrating the principle of a remote-center-of-motion mechanism according to Embodiment 2.

Reference is now made to FIG. 3, a schematic diagram illustrating the principle of a remote-center-of-motion mechanism 2 according to Embodiment 2. As shown in FIG. 3, the remote-center-of-motion mechanism 2 includes active components, driven components and transmission components. Specifically, the active components include a first connecting rod member 200, a second connecting rod member 201, a third connecting rod member 202, a fourth connecting rod member 203 and a slide block device 210. A first (here, lower) end of the first connecting rod member 200 is rotatably connected to a first (here, proximal) end of the second connecting rod member 201 via a first rotating shaft 220. A second (here, distal) end of the second connecting rod member 201 is rotatably connected to the slide block device 210 via a second rotating shaft 221. The third connecting rod member 202 is slidably connected to the slide block device 210 and the third connecting rod member 202 passes through the axis of the second rotating shaft 221. A second (here, upper) end of the third connecting rod member 202 is rotatably connected to a second (here, distal) end of the fourth connecting rod member 203 via a third rotating shaft 222. A first (here, proximal) end of the fourth connecting rod member 203 is rotatably connected to the first connecting rod member 200 via a fourth rotating shaft 223.

The driven components include a fifth connecting rod member 204, a sixth connecting rod member 205 and a seventh connecting rod member 206 connected in sequence. A first (here, lower) end of the fifth connecting rod member 204 is rotatably connected to the fourth connecting rod member 203 via a fifth rotating shaft 224, and a second (here, upper) end of the fifth connecting rod member 204 is rotatably connected to the sixth connecting rod member 205 via a sixth rotating shaft 225. A second (here, distal) end of the sixth connecting rod member 205 is rotatably connected to a second (here, upper) end of the seventh connecting rod member 206 via a seventh rotating shaft 226, and a first end (here, proximal) of the sixth connecting rod member 205 is rotatably connected to a second (here, upper) end of the first connecting rod member 200 via an eighth rotating shaft 227.

The transmission components include a first runner 230, a second runner 231, a third runner 232, a fourth runner 233 and a flexible element S2. The first runner 230 and the third connecting rod member 202 rotate about the third rotating shaft 222 synchronously. The second runner 231 is sleeved over the fourth rotating shaft 223, and the third runner 232 is sleeved over the eighth rotating shaft 227. The fourth runner 233 and the seventh connecting rod member 206 rotate about the seventh rotating shaft 226 synchronously. The flexible element S2 is fixedly connected to each of the first runner 230 and the fourth runner 233 and is wound around and passes the second runner 231 and the third runner 232 from sides of the second runner 231 and the third runner 232 away from the seventh connecting rod member 206, to form a closed transmission loop. The first runner 230 is equal to the fourth runner 233 in diameter, and the third runner 232 is equal to the second runner 231 in diameter.

The winding path of the flexible element S2 can form angles similar to complementary wrap angles of a parallelogram. That is, the flexible element S2 passes through the third runner 232 and the second runner 231 from sides of the third runner 232 and the second runner 231 away from the seventh connecting rod member 206, and forms a first wrap angle with the third runner 232 and a second wrap angle with the second runner 231. When a driving torque is acted on the first connecting rod member 200 or the slide block device 210, or when a driving torque is acted on the fourth connecting rod member 203 or the sixth connecting rod member 205, the change value of the first wrap angle equals to the change value of the second wrap angle in number.

In this Embodiment, a forward path and a return path of the flexible element S2 is formed at the same side of the third runner 232 and the second runner 231. That is, the forward path and the return path of the flexible element S2 shares a same set of runners, i.e., the third runner 232 and the second runner 231, which are equal in diameter. In other embodiments, the forward path and the return path of the flexible element S2 may use respective sets of runners, i.e. each of the third runner 232 and the second runner 231 comprises two runners forming two sets of runners. That is, the third runner 232 shown in FIG. 3 is replaced with a third runner A and a third runner B, and the second runner 231 shown in FIG. 3 is replaced with a second runner A and a second runner B. The third runner A and the second runner A constitute one set of runners, and the third runner B and the second runner B constitute the other set of runners. The forward path of the flexible element S2 may be constrained along one side of each of the third runner A and the second runner A, while the return path of the flexible element S2 may be constrained along one side of the third runner B and the second runner B. The third runner A is equal to the second runner A in diameter, and the third runner B is equal to the second runner B in diameter. The diameter of the third runner A and the diameter of the third runner B may be equal or not. On the other hand, the second runner 231 may be fixedly or rotatably connected to the fourth rotating shaft 223, i.e. relative motion is allowed between the second runner 231 and the fourth rotating shaft 223. The third runner 232 is connected to the eighth rotating shaft 227 in a similar manner.

In this Embodiment, the first runner 230 may be fixedly connected to the third connecting rod member 202 so as to achieve synchronous rotation of the first runner 230 and the third connecting rod member 202 about the third rotating shaft 222. Alternatively, each of the first runner 230 and the third connecting rod member 202 may be fixedly connected to the third rotating shaft 222 so that the first runner 230 and the third connecting rod member 202 rotate about the third rotating shaft 222 is achieved.

A parallelogram can be formed by connecting virtual lines between the axis of the fourth rotating shaft 223, the axis of the fifth rotating shaft 224, the axis of the sixth rotating shaft 225 and the axis of the eighth rotating shaft 227.

The distance between the axis of the first rotating shaft 220 and the axis of the fourth rotating shaft 223 is in a first ratio to the distance between the axis of the first rotating shaft 220 and eighth rotating shaft 227, and the distance between the axis of the third rotating shaft 222 and the axis of the fourth rotating shaft 223 is in a second ratio to the distance between the axis of the eighth rotating shaft 227 and the axis of seventh rotating shaft 226. The first ratio is configured to be equal to the second ratio. Only when the first ratio is equal to the second ratio, can it be ensured that variation of the angle formed by the third connecting rod member 202 and the fourth connecting rod member 203 of the remote-center-of-motion mechanism 2 equals to variation of the angle formed by the sixth connecting rod member 205 and the seventh connecting rod member 206 of the remote-center-of-motion mechanism 2 during the movement. In embodiments, each of the first ratio and the second ratio preferably ranges from 1/12 to 1/2. In this Embodiment, each of the first and second ratios is 1/6.

The first connecting line is formed by the virtual connecting line between the axis of the fifth rotating shaft 224 and the axis of the fourth rotating shaft 223, and the second connecting line is formed by the virtual connecting line between the axis of the fourth rotating shaft 223 and the axis of the third rotating shaft 222. The first angle (having a first angular value) is formed by the first connecting line and the second connecting line. The third connecting line is formed by the virtual connecting line between the axis of the second rotating shaft 221 and the axis of the third rotating shaft 222. The second angle (having a second angular value) is formed by the third connecting line and the seventh connecting rod member 206. The fourth connecting line is formed by the virtual connecting line between the axis of the first rotating shaft 220 and the axis of the fourth rotating shaft 223, and the fifth connecting line is formed by the virtual connecting line between the axis of the first rotating shaft 220 and the axis of the eighth rotating shaft 227. The third angle (having a third angular value) is formed by the fourth connecting line and the fifth connecting line. The first angle, the second angle and the third angle are configured to be equal.

In embodiments, the first angle, the second angle and the third angle preferably range from −30° to 30°. In this Embodiment, the first angle, the second angle and the third angle are set to 0°. That is, the third rotating shaft 222, the fourth rotating shaft 223 and the fifth rotating shaft 224 are situated on a same straight virtual line, i.e. the fourth connecting rod member 203 is a straight bar. Additionally, the first rotating shaft 220, the fourth rotating shaft 223 and the eighth rotating shaft 227 are also situated on a same straight virtual line, i.e. the first connecting rod member 200 is also a straight bar. The third connecting rod member 202 is also a straight bar, and the seventh connecting rod member 206 is parallel to the third connecting rod member 202. That is, the seventh connecting rod member 206 is parallel to the virtual connecting line between the axis of the second rotating shaft 221 and the axis of the third rotating shaft 222.

In this Embodiment, the remote center of motion D2 is the intersection of the axial line of the seventh connecting rod member 206 and an imaginary extending line of the connecting line between the axis of the first rotating shaft 220 and the axis of the second rotating shaft 221. The first or second ratio is also equal to the ratio of the moving distance of the first (lower) end of the third connecting rod member 202 of the active components relative to the second rotating shaft 221 to the moving distance of the first (lower) end of the seventh connecting rod member 206 of the driven components relative to the remote center of motion D2 during the movement of the remote-center-of-motion mechanism 1.

Figure 4:
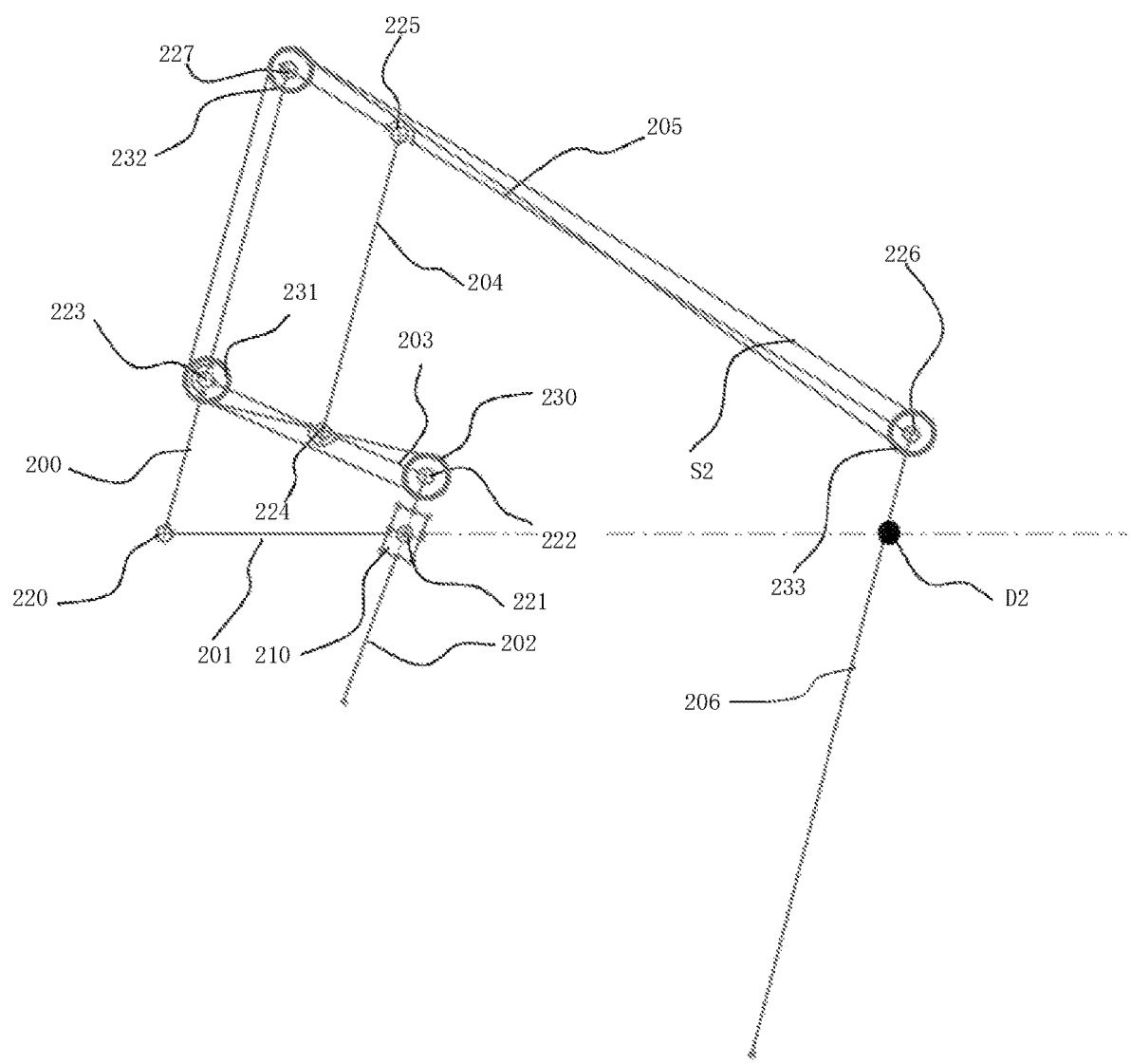
FIG. 4 is a schematic diagram illustrating the remote-center-of-motion mechanism of FIG. 3 after a movement.

Referring to FIGS. 3 and 4, taking the second connecting rod member 201 as a reference line, the remote-center-of-motion mechanism 2 is able to rotate around the remote center of motion D2 when a driving torque is acted on the first connecting rod member 200 or the slide block device 210, and the remote-center-of-motion mechanism 2 is able to make telescopic movement relative to the remote center of motion D2 when a driving torque is exerted on the fourth connecting rod member 203 or the sixth connecting rod member 205. Further, the remote-center-of-motion mechanism 2 is able to rotate around the remote center of motion D2 as well as to make telescopic movement relative to the remote center of motion D2 when one driving torque is acted on the first connecting rod member 200 or the slide block device 210 and another driving torque is applied to the fourth connecting rod member 203 or the sixth connecting rod member 205. That is to say, the remote-center-of-motion mechanism 2 has two degrees of freedom of the rotational movement around remote center of motion D2 and the telescopic movement relative to remote center of motion D2.

Embodiment 3

Figure 5:
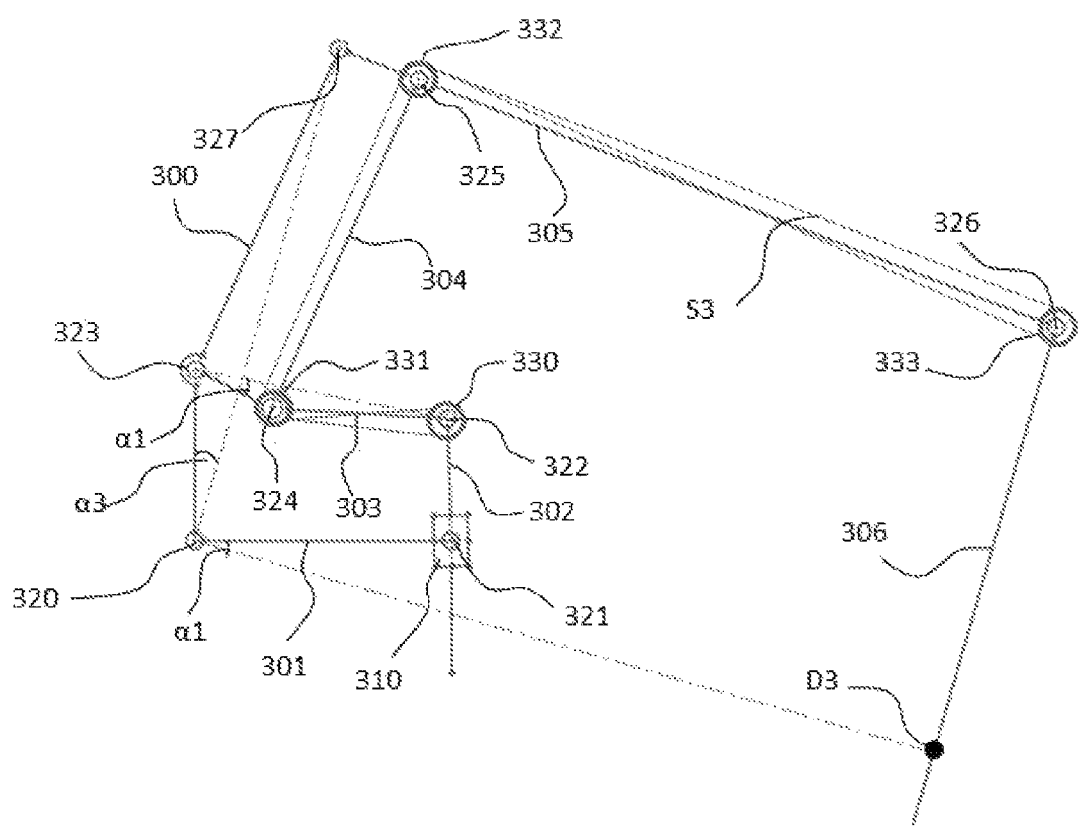
FIG. 5 is a schematic diagram illustrating the principle of a remote-center-of-motion mechanism according to Embodiment 3.

Reference is now made to FIG. 5, a schematic diagram illustrating the principle of a remote-center-of-motion mechanism according to Embodiment 3. As shown in FIG. 5, the remote-center-of-motion mechanism 3 includes active components, driven components and transmission components. Specifically, the active components include a first connecting rod member 300, a second connecting rod member 301, a third connecting rod member 302, a fourth connecting rod member 303 and a slide block device 310. A first (here, lower) end of the first connecting rod member 300 is rotatably connected to a first (here, proximal) end of the second connecting rod member 301 via a first rotating shaft 320. A second (here, distal) end of the second connecting rod member 301 is rotatably connected to the slide block device 310 via a second rotating shaft 321. The third connecting rod member 302 is slidably connected to the slide block device 310 and the third connecting rod member 302 passes through the axis of the second rotating shaft 321. A second (here, upper) end of the third connecting rod member 302 is rotatably connected to a second (here, distal) end of the fourth connecting rod member 303 via a third rotating shaft 322. A first (here, proximal) end of the fourth connecting rod member 303 is rotatably connected to the first connecting rod member 300 via a fourth rotating shaft 323.

The driven components include a fifth connecting rod member 304, a sixth connecting rod member 305 and a seventh connecting rod member 306 connected in sequence. A second (here, upper) end of the fifth connecting rod member 304 is rotatably connected to the sixth connecting rod member 305 via a sixth rotating shaft 325. A second (here, distal) end of the sixth connecting rod member 305 is rotatably connected to a second (here, upper) end of the seventh connecting rod member 306 via a seventh rotating shaft 326. Moreover, a first (here, lower) end of the fifth connecting rod member 304 is rotatably connected to the fourth connecting rod member 303 via the fifth rotating shaft 324, and a first (here, proximal) end of the sixth connecting rod member 305 is rotatably connected to a second (here, upper) end of the first connecting rod member 300 via an eighth rotating shaft 327.

The transmission components include a first runner 330, a second runner 331, a third runner 332, a fourth runner 333 and a flexible element S3. The first runner 330 and the third connecting rod member 302 rotate about the third rotating shaft 322 synchronously. The second runner 331 is sleeved over the fifth rotating shaft 324, and the third runner 332 is sleeved over the sixth rotating shaft 325. The fourth runner 333 and the seventh connecting rod member 306 rotate about the seventh rotating shaft 326 synchronously. The flexible element S3 is fixedly connected to each of the first runner 330 and the fourth runner 333 and is wound around and passes the second runner 331 and the third runner 332 through sides of the second runner 331 and the third runner 332 away from the seventh connecting rod member 306, to form a closed transmission loop. The first runner 330 is equal to the fourth runner 333 in diameter, and the third runner 332 is equal to the second runner 331 in diameter.

That is, the winding path of the flexible element S3 can form angles similar to complementary wrap angles of a parallelogram. In other words, the flexible element S3 passes through the third runner 332 and the second runner 331 from sides of the third runner 332 and the second runner 331 away from the seventh connecting rod member 306, and forms a first wrap angle with the third runner 332 and a second wrap angle with the second runner 331. When a driving torque is acted on the first connecting rod member 300 or the slide block device 310, or when a driving torque is acted on the fourth connecting rod member 303 or the sixth connecting rod member 305, the change value of the first wrap angle equals to the change value of the second wrap angle in number.

In this Embodiment, forward path and return path of the flexible element S3 are formed at the same side of the third runner 332 and the second runner 331. That is, the forward path and the return path of the flexible element S3 shares a same set of runners, i.e., the third runner 332 and the second runner 331, which are equal in diameter. In other embodiments, the forward path and the return path of the flexible element S3 may also use respective sets of runners, i.e. each of the third runner 332 and the second runner 331 comprises two runners forming two sets of runners. That is, the third runner 332 shown in FIG. 5 is replaced with a third runner A and a third runner B, and the second runner 331 shown in FIG. 5 is replaced with a second runner A and a second runner B. The third runner A and the second runner A constitute one set of runner, and the third runner B and the second runner B constitute the other set of runner. The forward path of the flexible element S3 may be constrained along one side of the third runner A and the second runner A, while the return path of the flexible element S3 may be constrained along one side of the third runner B and the second runner B. The third runner A is equal to the second runner A in diameter, and the third runner B is equal to the second runner B in diameter. The diameter of the third runner A and the diameter of the third runner B may be equal or not. On the other hand, the second runner 331 may be fixedly or rotatably connected to the fifth rotating shaft 324, i.e. relative motion is allowed between the second runner 331 and the fifth rotating shaft 324. The third runner 332 is connected to the sixth rotating shaft 325 in a similar manner.

In this Embodiment, the first runner 330 may be fixedly connected to the third connecting rod member 302 so as to achieve synchronous rotation of the first runner 330 and the third connecting rod member 302 about the third rotating shaft 322. Alternatively, each of the first runner 330 and the third connecting rod member 302 may be fixedly connected to the third rotating shaft 322 so that synchronous rotation of the first runner 330 and the third connecting rod member 302 rotating about the third rotating shaft 322 is achieved.

A parallelogram can be formed by connecting virtual lines between the axis of the fourth rotating shaft 323, the axis of the fifth rotating shaft 324, the axis of the sixth rotating shaft 325 and the axis of the eighth rotating shaft 327.

The distance between the axis of the first rotating shaft 320 and the axis of the fourth rotating shaft 323 is in a first ratio to the distance between the axis of the first rotating shaft 320 and the axis of the eighth rotating shaft 327, and the distance between the axis of the third rotating shaft 322 and the axis of the fourth rotating shaft 323 is in a second ratio to the distance between the axis of the eighth rotating shaft 327 and the axis of seventh rotating shaft 326. The first ratio is configured to be equal to the second ratio. Only when the first ratio is equal to the second ratio, can it be ensured that variation of the angle formed by the third connecting rod member 302 and the fourth connecting rod member 303 of the remote-center-of-motion mechanism 3 equals to the variation of the angle between the sixth connecting rod member 305 and the seventh connecting rod member 306 of the remote-center-of-motion mechanism 3 during the movement. In embodiments, each of the first ratio and the second ratio preferably ranges from 1/12 to 1/2. In this Embodiment, each of the first ratio and the second ratio is 1/6.

The first connecting line is formed by the virtual connecting line between the axis of the fifth rotating shaft 324 and the axis of the fourth rotating shaft 323, and the second connecting line is formed by the virtual connecting line between the axis of the fourth rotating shaft 323 and the axis of the third rotating shaft 322. The first angle a1 (having a first angular value) is formed by the first connecting line and the second connecting line. The third connecting line is formed by the virtual connecting line between the axis of the second rotating shaft 321 and the axis of the third rotating shaft 322. The second angle (having a second angular value) is formed by the third connecting line and the axial line of the seventh connecting rod member 306. The fourth connecting line is formed by the virtual connecting line between the axis of the first rotating shaft 320 and the axis of the fourth rotating shaft 323, and the fifth connecting line is formed by the virtual connecting line between the axis of the first rotating shaft 320 and the axis of the eighth rotating shaft 327. The third angle a3 (having a third angular value) is formed by the fourth connecting line and the fifth connecting line. The first angle a1, the second angle and the third angle a3 are configured to be equal.

Further, according to the embodiments, the sign of the first angle a1, the second angle and the third angle a3 is determined as follow: if the first connecting line coincides with the second connecting line after rotating counterclockwise about the axis of the fourth rotating shaft 323 by the first angular value, then the corresponding first angle a1 is positive, and if the first connecting line coincides with the second connecting line after rotating clockwise about the axis of the fourth rotating shaft 323 by the first angular value, then the corresponding first angle a1 is negative. Assuming that the first parallel line is a virtual straight line paralleling to the seventh connecting rod member 306 and passing through the axis of the second rotating shaft 321, if the third connecting line coincides with the first parallel line after rotating clockwise or counterclockwise about the axis of the second rotating shaft 321 by the second angular value, then the corresponding second angle is positive or negative, respectively; and if the fourth connecting line coincides with the fifth connecting line after rotating clockwise or counterclockwise about the axis of the first rotating shaft 320 by the third angular value, then the corresponding third angle a3 is positive or negative, respectively. In embodiments, a remote-center-of-motion mechanism can be achieved only when the first angle a1, the second angle and the third angle a3 are not only equal in absolute value but also are both positive or negative. It will be appreciated by those skilled in the art that, if an angle of a mechanism has a negative angular value whereas its positive angular value equivalent of the said negative angular value (i.e., 360° minus the absolute value of the angular value of an angle) equals to the angular values of the other two angles, then the said mechanism falls into the scope of the embodiments. Similarly, if an angle of a mechanism has a positive angular value whereas its negative angular value equivalent of the said positive angular value (i.e., the absolute value of the angular value of an angle minus 360°) equals to the angular values of the other angles, then the said mechanism falls into the protection scope of the embodiments.

In embodiments, the first angle, the second angle and the third angle preferably range from −30° to 30°. In this embodiment, the first angle a1, the second angle and the third angle a3 are all positive, and particularly are 15°, i.e. the fourth connecting rod member 303 is a flexed rod.

Specifically, the fourth connecting rod member 303 includes a first connecting rod member section between the fourth rotating shaft 323 and the fifth rotating shaft 324, and a second connecting rod member section between the third rotating shaft 322 and the fifth rotating shaft 324, wherein the first connecting rod member section is fixedly connected to the second connecting rod member section with a flexed angle. In FIG. 5, each of the first connecting rod member section and the second connecting rod member section is a straight bar, and the fifth rotating shaft 324 is situated below the virtual connecting line between the axis of the third rotating shaft 322 and the axis of the fourth rotating shaft 323 (i.e., the first angle a1 is formed by the first connecting line rotating counterclockwise about the axis of the fourth rotating shaft 323 by the first angular value and then coinciding with the second connecting line). Similarly, the first connecting rod member 300 is a flexed rod. Specifically, the first connecting rod member 300 includes a third connecting rod member section between the first rotating shaft 320 and the fourth rotating shaft 323, and a fourth connecting rod member section between the fourth rotating shaft 323 and the eighth rotating shaft 327, wherein the third connecting rod member section is fixedly connected to the fourth connecting rod member section with a flexed angle. In FIG. 5, each of the third connecting rod member section and the fourth connecting rod member section is a straight bar, and the fourth rotating shaft 323 is situated on the left side or proximal end of the virtual connecting line between the axis of the first rotating shaft 320 and the axis of the eighth rotating shaft 327 (i.e., the third angle a3 is formed by the fourth connecting line rotating clockwise about the axis of the third rotating shaft 322 by the third angular value and then coinciding with the fifth connecting line). Similarly, in FIG. 5, assuming that the first parallel line is a virtual straight line paralleling to the seventh connecting rod member 306 and passing through the axis of the second rotating shaft 321, the axis of the third rotating shaft 322 is located at the left side of the first parallel line (i.e., the second angle is formed by the third connecting line rotating clockwise about the axis of the second rotating shaft 321 by the second angular value and then coinciding with the first parallel line). In this Embodiment, the sixth connecting line, formed by the virtual connecting line between the axis of the first rotating shaft 320 and the axis of the second rotating shaft 321, rotates clockwise by the first angle a1 with the axis of the first rotating shaft 320 as the end point, and then intersects with the axial line of the seventh connecting rod member 306, wherein the intersection is the remote center of motion D3.

In an alternative embodiment, the fifth rotating shaft 324 may be situated above the connecting virtue line between the axis of the third rotating shaft 322 and the axis of the fourth rotating shaft 323 (i.e., the first angle a1 is formed by the first connecting line rotating clockwise about the axis of the fourth rotating shaft 323 by the first angular value and then coinciding with the second connecting line). In this case, accordingly, the fourth rotating shaft 323 is situated at the right side or distal end of the virtual connecting line between the axis of the first rotating shaft 320 and the axis of the eighth rotating shaft 327 (i.e., the third angle a3 is formed by the fourth connecting line rotating counterclockwise about the axis of the first rotating shaft 320 by the third angular value and then coinciding with the fifth connecting line), and the axis of the third rotating shaft 322 is located at the right side of the first parallel line (i.e., the second angle is formed by the third connecting line rotating counterclockwise about the axis of the second rotating shaft 321 by the second angular value and then coinciding with the first parallel line). In this case, the sixth connecting line, formed by the virtual connecting line between the axis of the first rotating shaft 320 and the axis of the second rotating shaft 321, rotates counterclockwise by the first angle a1 with the axis of the first rotating shaft 320 as the end point, and then intersects with the axial line of the seventh connecting rod member 306, wherein the intersection is the remote center of motion D3.

The first ration or the second ratio is also equal to the ratio of the moving distance of the first (lower) end of the third connecting rod member 302 of the active components relative to the second rotating shaft 321 to the moving distance of the first (lower) end of the seventh connecting rod member 306 of the driven components relative to the remote center of motion D3 during the movement of the remote-center-of-motion mechanism 3.

With continued reference to FIG. 5, taking the second connecting rod member 301 as a reference line in operation, the remote-center-of-motion mechanisms 3 is able to rotate around the remote center of motion D3 when a driving torque is acted on the first connecting rod member 300 or the slide block device 310, and the remote-center-of-motion mechanism 3 is able to make telescopic movement relative to the remote center of motion D3 when a driving torque is exerted on the fourth connecting rod member 303 or the sixth connecting rod member 305. Further, the remote-center-of-motion mechanism 3 is able to rotate around the remote center of motion D3 as well as to make telescopic movement relative to the remote center of motion D3 when one driving torque is acted on the first connecting rod member 300 or the slide block device 310 and another driving torque is applied to the fourth connecting rod member 303 or the sixth connecting rod member 305. That is to say, the remote-center-of-motion mechanism 3 has two degrees of freedom of the rotational movement around remote center of motion D3 and the telescopic movement with respect to remote center of motion D3.

Embodiment 4

Figure 6:
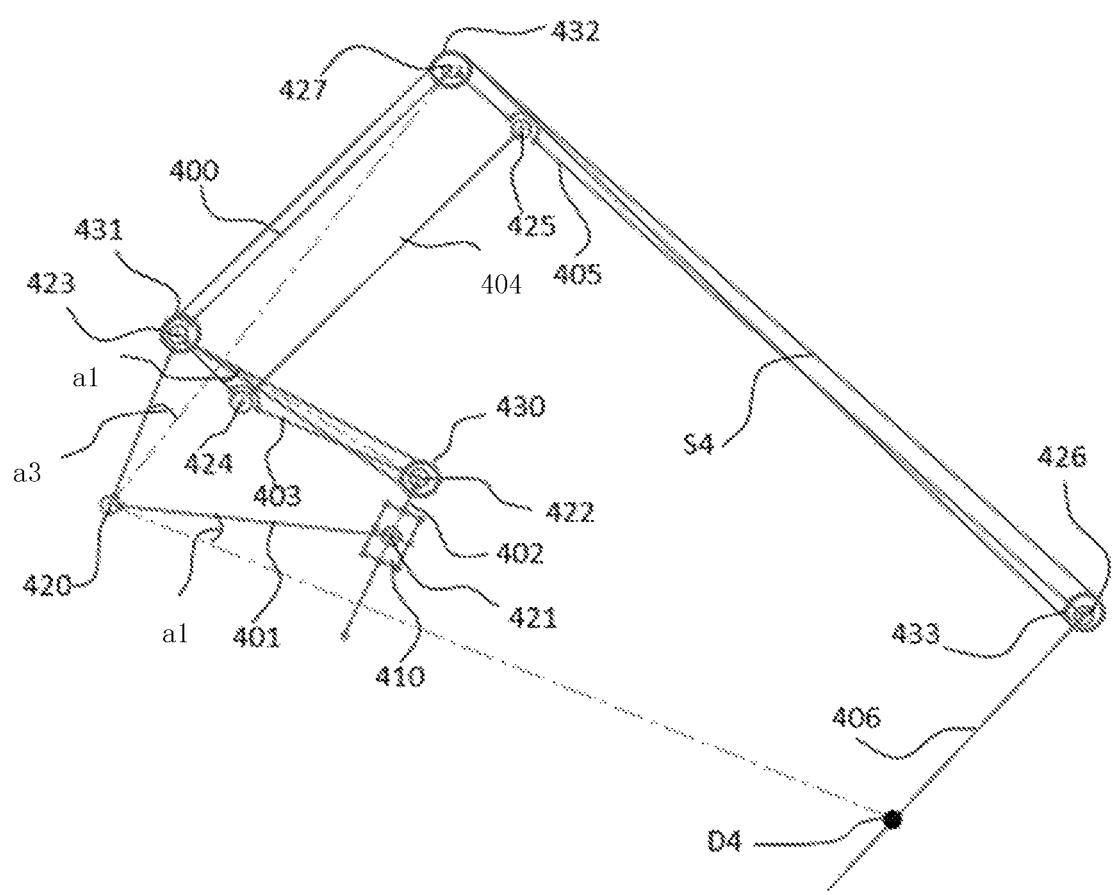
FIG. 6 is a schematic diagram illustrating the principle of a remote-center-of-motion mechanism according to Embodiment 4.

Reference is now made to FIG. 6, a schematic diagram illustrating the principle of a remote-center-of-motion mechanism according to Embodiment 4. As shown in FIG. 6, the remote-center-of-motion mechanism 4 includes active components, driven components and transmission components. Specifically, the active components include a first connecting rod member 400, a second connecting rod member 401, a third connecting rod member 402, a fourth connecting rod member 403 and a slide block device 410. A first (here, lower) end of the first connecting rod member 400 is rotatably connected to a first (here, proximal) end of the second connecting rod member 401 via a first rotating shaft 420. A second (here, distal) end of the second connecting rod member 401 is rotatably connected to the slide block device 410 via a second rotating shaft 421. The third connecting rod member 402 is slidably connected to the slide block device 410 and passes through the axis of the second rotating shaft 421. A second (here, upper) end of the third connecting rod member 402 is rotatably connected to a second (here, distal) end of the fourth connecting rod member 403 via a third rotating shaft 422. A first (here, proximal) end of the fourth connecting rod member 403 is rotatably connected to the first connecting rod member 400 via a fourth rotating shaft 423.

The driven components include a fifth connecting rod member 404, a sixth connecting rod member 405 and a seventh connecting rod member 406 connected in sequence. A first (here, lower) end of the fifth connecting rod member 404 is rotatably connected to the fourth connecting rod member 403 via a fifth rotating shaft 424, and a second (here, upper) end of the fifth connecting rod member 404 is rotatably connected to the sixth connecting rod member 405 via a sixth rotating shaft 425. A second (here, distal) end of the sixth connecting rod member 405 is rotatably connected to a second (here, upper) end of the seventh connecting rod member 406 via a seventh rotating shaft 426, and a first (here, proximal) end of the sixth connecting rod member 405 is rotatably connected to a second (here, upper) end of the first connecting rod member 400 via an eighth rotating shaft 427.

The transmission components include a first runner 430, a second runner 431, a third runner 432, a fourth runner 433 and a flexible element S4. The first runner 430 and the third connecting rod member 402 rotate about the third rotating shaft 422 synchronously. The second runner 431 is sleeved over the fourth rotating shaft 423, and the third runner 432 is sleeved over the eighth rotating shaft 427. The fourth runner 433 and the seventh connecting rod member 406 rotate about the seventh rotating shaft 426 synchronously. The flexible element S4 is fixedly connected to each of the first runner 430 and the fourth runner 433 and is wound around and passes the second runner 431 and the third runner 432 through the sides of the second runner 431 and the third runner 432 away from the seventh connecting rod member 406, to form a closed transmission loop. The first runner 430 is equal to the fourth runner 433 in diameter, and the third runner 432 is equal to the second runner 431 in diameter.

The winding path of the flexible element S4 can form angles similar to complementary wrap angles of a parallelogram. That is, the flexible element S4 passes through the third runner 432 and the second runner 431 from sides of the third runner 432 and the second runner 431 away from the seventh connecting rod member 406, and forms a first wrap angle with the third runner 432 and a second wrap angle with the second runner 431. When a driving torque is acted on the first connecting rod member 400 or the slide block device 410, or when a driving torque is exerted on the fourth connecting rod member 403 or the sixth connecting rod member 405, the change value of the first wrap angle equals to the change value of the second wrap angle in number.

In this Embodiment, a forward path and a return path of the flexible element S4 are formed at the same side of the third runner 432 and the second runner 431 away from the seventh connecting rod member. That is, the forward path and return path of the flexible element S4 shares a same set of runners, i.e., the third runner 432 and the second runner 431, which are equal in diameter. In other embodiments, the forward path and return path of the flexible element S4 may also use respective sets of runners, i.e. each of the third runner 432 and the second runner 431 comprises two runners forming two sets of runners. That is, the third runner 432 shown in FIG. 6 is replaced with a third runner A and a third runner B, and the second runner 431 shown in FIG. 6 is replaced with a second runner A and a second runner B. The third runner A and the second runner A constitute one set of runners, and the third runner B and the second runner B constitute the other set of runners. The forward path of the flexible element S4 may be constrained along one side of the third runner A and the second runner A, while the return path of the flexible element S4 may be constrained along one side of the third runner B and the second runner B. The third runner A is equal to the second runner A in diameter, and the third runner B is equal to the second runner B in diameter. The diameter of the third runner A and the third runner B may be equal or not. The second runner 431 may be fixedly or rotatably connected to the fourth rotating shaft 423, i.e. relative motion is allowed between the second runner 431 and the fourth rotating shaft 423. The third runner 432 is connected to the eighth rotating shaft 427 in a similar manner.

In this Embodiment, the first runner 430 may be fixedly connected to the third connecting rod member 402 so as to achieve synchronous rotation of the first runner 430 and the third connecting rod member 402 about the third rotating shaft 422. Alternatively, each of the first runner 430 and the third connecting rod member 402 may be fixedly connected to the third rotating shaft 422 so that synchronous rotation of the first runner 430 and the third connecting rod member 402 about the third rotating shaft 422 is achieved.

A parallelogram can be formed by connecting virtual lines between the axis of the fourth rotating shaft 423, the axis of the fifth rotating shaft 424, the axis of the sixth rotating shaft 425 and the axis of the eighth rotating shaft.

The distance between the axis of the first rotating shaft 420 and the axis of the fourth rotating shaft 423 is in a first ratio to the distance between the axis of the first rotating shaft 420 and the axis of eighth rotating shaft 427, and the distance between the axis of the third rotating shaft 422 and the axis of the fourth rotating shaft 423 is in a second ratio to the distance between the axis of the eighth rotating shaft 427 and the axis of seventh rotating shaft 426. The first ratio is configured to be equal to the second ratio. Only when the first ratio is equal to the second ratio, can it be ensured that variation of the angle formed by the third connecting rod member 402 and the fourth connecting rod member 403 of the remote-center-of-motion mechanism 4 equals to the variation of the angle formed by the sixth connecting rod member 405 and the seventh connecting rod member 406 of the remote-center-of-motion mechanism 4 during the movement. In embodiments, each of the first ratio and the second ratio preferably ranges from 1/12 to 1/2. In this Embodiment, each of the first ratio and the second ratio is 1/6.

The first connecting line is formed by the virtual connecting line between the axis of the fifth rotating shaft 424 and the axis of the fourth rotating shaft 423 and the second connecting line is formed by the virtual connecting line between the axis of the fourth rotating shaft 423 and the axis of the third rotating shaft 422. The first angle a1 (having a first angular value) is formed by the first connecting line and the second connecting line. The third connecting line is formed by the virtual connecting line between the axis of the second rotating shaft 421 and the axis of the third rotating shaft 422. The second angle (having a second angular value) is formed by the third connecting line and the seventh connecting rod member 406. The fourth connecting line is formed by the virtual connecting line between the axis of the first rotating shaft 420 and the axis of the fourth rotating shaft 423, and the fifth connecting line is formed by the virtual connecting line between the axis of the first rotating shaft 420 and the axis of the eighth rotating shaft 427. The third angle a3 (having a third angular value) is formed by the fourth connecting line and the fifth connecting line. The first angle a1, the second angle and the third angle a3 are configured to be equal. Since the third connecting rod member 402 passes through the axis of the second rotating shaft 421, the second angle formed by the seventh connecting rod member 406 and the virtual connecting line between the axis of the second rotating shaft 421 and the axis of the third rotating shaft 422 is also the angle formed by the seventh connecting rod member 406 and the third connecting rod member 402. In this Embodiment, the third connecting rod member 402 is a straight bar.

Further, according to the embodiments, the sign of the first angle a1, the second angle and the third angle a3 is determined as follow: if the first connecting line coincides with the second connecting line after rotating counterclockwise about the axis of the fourth rotating shaft 423 by the first angular value, then the corresponding first angle a1 is positive, and if the first connecting line coincides with the second connecting line after rotating clockwise about the axis of the fourth rotating shaft 423 by the first angular value, then the corresponding first angle is negative. Assuming that the first parallel line is a virtual straight line paralleling to the axial line of the seventh connecting rod member 406 and passing through the axis of the second rotating shaft 421, if the third connecting line coincides with the first parallel line after rotating clockwise or counterclockwise about the axis of the second rotating shaft 421 by the second angular value, then the corresponding second angle is positive or negative, respectively; and if the fourth connecting line coincides with the fifth connecting line after rotating clockwise or counterclockwise about the axis of the first rotating shaft 420 by the third angular value, then the corresponding third angle a3 is positive or negative, respectively. According to the embodiments, a remote-center-of-motion mechanism can be achieved only when the first angle a1, the second angle and the third angle a3 are not only equal in absolute value but also are both positive or negative. It will be appreciated by those skilled in the art that, if an angle of a mechanism has a negative angular value whereas its positive angular value equivalent of the said negative angular value (i.e., 360° minus the absolute value of the angular value of an angle) equals to the angular values of the other two angles, then the said mechanism falls into the protection scope of the embodiments. Similarly, if an angle of a mechanism has a positive angular value whereas its negative angular value equivalent of the said positive angular value (i.e., the absolute value of the angular value of an angle minus 360°) equals to the angular values of the other angles, then the said mechanism falls into the protection scope of the embodiments.

In embodiments, the first angle, the second angle and the third angle preferably range from −30° to 30°. In this embodiment, the first angle a1, the second angle and the third angle a3 are all positive, and particularly are 15°, i.e. the fourth connecting rod member 403 is a flexed rod. Specifically, the fourth connecting rod member 403 includes a first connecting rod member section between the fourth rotating shaft 423 and the fifth rotating shaft 424, and a second connecting rod member section between the third rotating shaft 422 and the fifth rotating shaft 424, wherein the first connecting rod member section is fixedly connected to the second connecting rod member section with a flexed angle. In FIG. 6, each of the first connecting rod member section and the second connecting rod member section is a straight bar, and the fifth rotating shaft 424 is situated below the virtual connecting line between the axis of the third rotating shaft 422 and the axis of the fourth rotating shaft 423 (i.e., the first angle a1 is formed by the first connecting line rotating counterclockwise about the axis of the fourth rotating shaft 423 by the first angular value and then coinciding with the second connecting line). Similarly, the first connecting rod member 400 is a flexed rod. Specifically, the first connecting rod member 400 includes a third connecting rod member section between the first rotating shaft 420 and the fourth rotating shaft 423, and a fourth connecting rod member section between the fourth rotating shaft 423 and the eighth rotating shaft 427, wherein the third connecting rod member section is fixedly connected to the fourth connecting rod member section with a flexed angle. In FIG. 6, each of the third connecting rod member section and the fourth connecting rod member section is a straight bar, and the fourth rotating shaft 423 is situated at the left side or proximal end of the virtual connecting line between the axis of the first rotating shaft 420 and the axis of the eighth rotating shaft 427 (i.e., the third angle a3 is formed by the fourth connecting line rotating clockwise about the axis of the third rotating shaft 422 by the third angular value and then coinciding with the fifth connecting line). Similarly, in FIG. 6, assuming that the first parallel line is a virtual straight line paralleling to the axial line of the seventh connecting rod member 406 and passing through the axis of the second rotating shaft 421, the axis of the third rotating shaft 422 is located at the left side of the first parallel line (i.e., the second angle is formed by the third connecting line rotating clockwise about the axis of the second rotating shaft 421 by the second angular value and then coinciding with the first parallel line). In this Embodiment, the sixth connecting line, formed by the virtual connecting line between the axis of the first rotating shaft 420 and the axis of the second rotating shaft 421, rotates clockwise by the first angle a1 with the axis of the first rotating shaft 420 as the end point, and then intersects with the axial line of the seventh connecting rod member 406, wherein the intersection is the remote center of motion D4.

In an alternative embodiment, the fifth rotating shaft 424 may be situated above the virtual connecting line between the axis of the third rotating shaft 422 and the axis of the fourth rotating shaft 423 (i.e., the first angle a1 is formed by the first connecting line rotating clockwise about the axis of the fourth rotating shaft 423 by the first angular value and then coinciding with the second connecting line). In this case, accordingly, the fourth rotating shaft 423 is situated at the right side or distal end of the virtual connecting line between the axis of the first rotating shaft 420 and the axis of the eighth rotating shaft 427 (i.e., the third angle a3 is formed by the fourth connecting line rotating counterclockwise about the axis of the first rotating shaft 420 by the third angular value and then coinciding with the fifth connecting line), and the axis of the third rotating shaft 422 is located at the right side of the first parallel line (i.e., the second angle is formed by the third connecting line rotating counterclockwise about the axis of the second rotating shaft 421 by the second angular value and then coinciding with the first parallel line). In this case, the sixth connecting line, formed by the virtual connecting line between the axis of the first rotating shaft 420 and the axis of the second rotating shaft 421, rotates counterclockwise by the first angle a1 with the axis of the first rotating shaft 420 as end point, and then intersects with the axial line of the seventh connecting rod member 406, wherein the intersection is the remote center of motion D4.

The first ratio or the second ratio is also equal to the ratio of the moving distance of the first (lower) end of the third connecting rod member 402 of the active components relative to the second rotating shaft 421 to the moving distance of the first (lower) end of the seventh connecting rod member 406 of the driven components relative to the remote center of motion D4 during the movement of the remote-center-of-motion mechanism 4.

With continued reference to FIG. 6, taking the second connecting rod member 401 as a reference line in operation, the remote-center-of-motion mechanism 4 is able to rotate around the remote center of motion D4 when a driving torque is acted on the first connecting rod member 400 or the slide block device 410, and the remote-center-of-motion mechanisms 4 is able to make telescopic movement relative to the remote center of motion D4 when a driving torque is exerted on the fourth connecting rod member 403 or the sixth connecting rod member 405. Further, the remote-center-of-motion mechanisms 4 is able to rotate around the remote center of motion D4 as well as to make telescopic movement relative to the remote center of motion D4 when one driving torque is acted on the first connecting rod member 400 or the slide block device 410 and another driving torque is applied to the fourth connecting rod member 403 or the sixth connecting rod member 405. That is to say, the remote-center-of-motion mechanism 4 has two degrees of freedom of the rotational movement around remote center of motion D3 and the telescopic movement with respect to remote center of motion D4.

Embodiment 5

Figure 7:
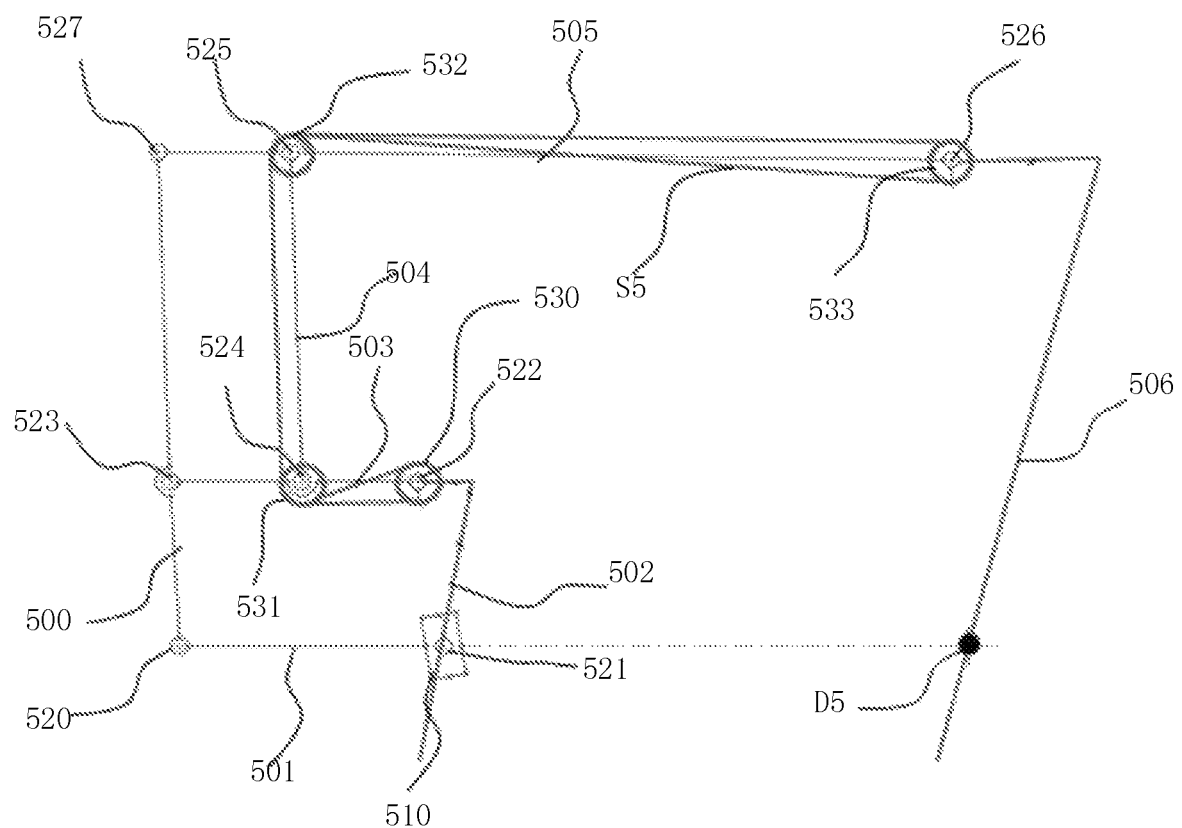
FIG. 7 is a schematic diagram illustrating the principle of a remote-center-of-motion mechanism according to Embodiment 5.

Reference is now made to FIG. 7, a schematic diagram illustrating the principle of a remote-center-of-motion mechanism according to Embodiment 5. As shown in FIG. 7, the remote-center-of-motion mechanism 5 includes active components, driven components and transmission components. Specifically, the active components include a first connecting rod member 500, a second connecting rod member 501, a third connecting rod member 502, a fourth connecting rod member 503 and a slide block device 510. A first (here, lower) end of the first connecting rod member 500 is rotatably connected to a first (here, proximal) end of the second connecting rod member 501 via a first rotating shaft 520. A second (here, distal) end of the second connecting rod member 501 is rotatably connected to the slide block device 510 via a second rotating shaft 521. The third connecting rod member 502 is slidably connected to the slide block device 510 and the third connecting rod member 502 passes through the axis of the second rotating shaft 521. A second (here, upper) end of the third connecting rod member 502 is rotatably connected to a second (here, distal) end of the fourth connecting rod member 503 via a third rotating shaft 522. A first (here, proximal) end of the fourth connecting rod member 503 is rotatably connected to the first connecting rod member 500 via a fourth rotating shaft 523. The third connecting rod member 502 passes through the axis of the second rotating shaft 521.

The driven components include a fifth connecting rod member 504, a sixth connecting rod member 505 and a seventh connecting rod member 506 connected in sequence. A first (here, lower) end of the fifth connecting rod member 504 is rotatably connected to the fourth connecting rod member 503 via a fifth rotating shaft 524, and a second (here, upper) end of the fifth connecting rod member 504 is rotatably connected to the sixth connecting rod member 505 via a sixth rotating shaft 525. A second (here, distal) end of the sixth connecting rod member 505 is rotatably connected to a second (here, upper) end of the seventh connecting rod member 506 via a seventh rotating shaft 526, and a first (here, proximal) end of the sixth connecting rod member 505 is rotatably connected to a second (here, upper) end of the first connecting rod member 500 via an eighth rotating shaft 527.

The transmission components include a first runner 530, a second runner 531, a third runner 532, a fourth runner 533 and a flexible element S5. The first runner 530 and the third connecting rod member 502 rotate about the third rotating shaft 522 synchronously. The second runner 531 is sleeved over the fifth rotating shaft 524, and the third runner 532 is sleeved over the sixth rotating shaft 525. The fourth runner 533 and the seventh connecting rod member 506 rotate about the seventh rotating shaft 526 synchronously. The flexible element S5 is fixedly connected to each of the first runner 530 and the fourth runner 533 and is wound around and passes the second runner 531 and the third runner 532 through the sides of the second runner 531 and the third runner 532 away from the seventh connecting rod member, to form a closed transmission loop. The first runner 530 is equal to the fourth runner 533 in diameter, and the third runner 532 is equal to the second runner 531 in diameter.

That is, the winding path of the flexible element S5 can form angles similar to complementary wrap angles of a parallelogram. In other words, the flexible element S5 passes through the third runner 532 and the second runner 531 from the sides of the third runner 532 and the second runner 531 away from the seventh connecting rod member 506, and forms a first wrap angle with the third runner 532 and a second wrap angle with the second runner 531. When a driving torque is acted on the first connecting rod member 500 or the slide block device 510, or when a driving torque is acted on the fourth connecting rod member 503 or the sixth connecting rod member 505, the change value of the first wrap angle equals to the change value of the second wrap angle in number.

In this Embodiment, a forward path and a return path of the flexible element S5 are formed at the same side of the third runner 532 and the second runner 531 away from the seventh connecting rod member. That is, the forward path and return path of the flexible element S5 shares a same set of runners, i.e. the third runner 532 and the second runner 531, which are equal in diameter. In other embodiments, the forward path and the return path of the flexible element S5 may also use respective sets of runners, i.e. each of the third runner 532 and the second runner 531 comprises two runners forming two sets of runners. That is, the third runner 532 shown in FIG. 7 is replaced with a third runner A and a third runner B, and the second runner 531 shown in FIG. 7 is replaced with a second runner A and a second runner B. The third runner A and the second runner A constitute one set of runners, and the third runner B and the second runner B constitute the other set of runners. The forward path of the flexible element S5 may be constrained along one side of the third runner A and the second runner A away from the seventh connecting rod member, while the return path of the flexible element S5 may be constrained along one side of the third runner B and the second runner B away from the seventh connecting rod member. The third runner A is equal to the second runner A in diameter, and the third runner B is equal to the second runner B in diameter. The diameter of the third runner A and the diameter of the third runner B may be equal or not. The second runner 531 may be fixedly or rotatably connected to the fifth rotating shaft 524. In the latter case, relative motion is allowed between the second runner 531 and the fifth rotating shaft 524. The third runner 532 is connected to the sixth rotating shaft 525 in a similar manner.

In this Embodiment, the first runner 530 may be fixedly connected to the third connecting rod member 502 so as to achieve synchronous rotation of the first runner 530 and the third connecting rod member 502 about the third rotating shaft 522. Alternatively, each of the first runner 530 and the third connecting rod member 502 may be fixedly connected to the third rotating shaft 522 so that synchronous rotation of the first runner 530 and the third connecting rod member 502 about the third rotating shaft 522 is achieved.

A parallelogram can be formed by connecting virtue lines between the axis of the fourth rotating shaft 523, the axis of the fifth rotating shaft 524, the axis of the sixth rotating shaft 525 and the axis of the eighth rotating shaft 527.

The distance between the axis of the first rotating shaft 520 and the axis of the fourth rotating shaft 523 is in a first ratio to the distance between the axis of the first rotating shaft 520 and the axis of eighth rotating shaft 527, and the distance between the axis of the third rotating shaft 522 and the axis of the fourth rotating shaft 523 is in a second ratio to the distance between the axis of the eighth rotating shaft 527 and the axis of seventh rotating shaft 526. The first ratio is configured to be equal to the second ratio. Only when the first ratio is equal to the second ratio, can it be ensured that variation of the angle formed by the third connecting rod member 502 and the fourth connecting rod member 503 of the remote-center-of-motion mechanism 5 equals to variation of the angle formed by the sixth connecting rod member 505 and the seventh connecting rod member 506 of the remote-center-of-motion mechanism 5 during the movement. In embodiments, each of the first ratio and the second ratio preferably ranges from 1/12 to 1/2. In this Embodiment, each of the first ratio and the second ratio is 1/6.

The first connecting line is formed by the virtual connecting line between the axis of the fifth rotating shaft 524 and the axis of the fourth rotating shaft 523, and the second connecting line is formed by the virtual connecting line between the axis of the fourth rotating shaft 523 and the axis of the third rotating shaft 522. The first angle a1 (having a first angular value) is formed by the first connecting line and the second connecting line. The second angle (having a second angular value) is formed by the third connecting rod member 502 and the seventh connecting rod member 506. The fourth connecting line is formed by the virtual connecting line between the axis of the first rotating shaft 520 and the axis of the fourth rotating shaft 523, and the fifth connecting line is formed by the virtual connecting line between the axis of the first rotating shaft 520 and the axis of the eighth rotating shaft 527. The third angle a3 (having a third angular value) is formed by the fourth connecting line and the fifth connecting line. The first angle a1, the second angle and the third angle a3 are configured to be equal.

Further, in embodiments, the sign of the first angle a1, the second angle and the third angle a3 is determined as follow: if the first connecting line coincides with the second connecting line after rotating counterclockwise about the axis of the fourth rotating shaft 523 by the first angular value, then the corresponding first angle a1 is positive, and if the first connecting line coincides with the second connecting line after rotating clockwise about the axis of the fourth rotating shaft 523 by the first angular value, then the corresponding first angle is negative; and if the fourth connecting line coincides with the fifth connecting line after rotating clockwise or counterclockwise about the axis of the first rotating shaft 520 by the third angular value, then the corresponding third angle a3 is positive or negative, respectively.

In embodiments, the first angle, the second angle and the third angle preferably range from −30° to 30°. In this Embodiment, the first angle a1, the second angle and the third angle a3 are set to 0°. That is, the third rotating shaft 522, the fourth rotating shaft 523 and the fifth rotating shaft 524 are situated on the same straight virtual line, i.e. the fourth connecting rod member 503 is a straight bar, and the first rotating shaft 520, the fourth rotating shaft 523 and the eighth rotating shaft 527 are also situated on the same straight virtual line, i.e. the first connecting rod member 500 is also a straight bar.

In this Embodiment, the third connecting rod member 502 is a flexed rod and passes through the axis of the second rotating shaft 521 and the third rotating shaft 522, and the seventh connecting rod member 506 is also a flexed rod. Specifically, the third connecting rod member 502 includes a fifth connecting rod member section connected to the third rotating shaft 522, and a sixth connecting rod member section slidably connected to the slide block device 510, wherein the sixth connecting rod member section is a straight bar and passes through the axis of the second rotating shaft 521, and the fifth connecting rod member section is fixedly connected to the sixth connecting rod member section. The perpendicular segment between the axis of the third rotating shaft 522 and the sixth connecting rod member section defines a first segment. The seventh connecting rod member 506 includes a seventh connecting rod member section connected to the seventh rotating shaft 526 and an eighth connecting rod member section, wherein the eighth connecting rod member section is a straight bar and the seventh connecting rod member section is fixedly connected to the eighth connecting rod member section. The perpendicular segment between the axis of the seventh rotating shaft 526 and the eighth connecting rod member section defines a second segment. In this Embodiment, a length of the first segment is in a third ratio to a length of the second segment, and the third ratio is configured to be equal to the first ratio. That is, the third ratio preferably ranges from 1/12 to 1/2, more preferably is 1/6. Accordingly, the second angle is defined as: an angle formed by the second segment and a parallel line passing through the axis of the seventh rotating shaft 526 and paralleling to the first segment. Further, the sign of the second angle is determined as follow: if the parallel line coincides with the second segment after rotating clockwise or counterclockwise about the axis of the seventh rotating shaft 526 by the second angular value, then the corresponding second angle is positive or negative, respectively. This Embodiment provides only one example of the particular calculating method of the second angle, and there are other manners to define the calculating method and sign of the second angle. The length and orientation of the second segment can decide the position and orientation of the axial line of the eighth connecting rod member section. That is, the axial line of the eighth connecting rod member section is required to passing through one endpoint of the second segment as well as being perpendicular to the second segment in terms of the direction. The particular length of the eighth connecting rod member section is not limited, and may be decided based on practical applications. In embodiments, there is no specific limitation to the shape of each of the fifth connecting rod member section and the seventh connecting rod member section, which may be a straight bar, a curved rod, a flexed rod or a rod of other shape. In this Embodiment, there is also no specific limitation to the position of the connection between the seventh connecting rod member section and the eighth connecting rod member section.

In this embodiment, the fifth connecting rod member section is a straight bar, and the fourth angle (having a fourth angular value) is formed by the fifth connecting rod member section and the sixth connecting rod member section. Moreover, the sign of the fourth angle is determined as follow: the positive fourth angle is the angle formed by the fifth connecting rod member section rotating counterclockwise about the intersection of the fifth connecting rod member section and the sixth connecting rod member section by the fourth angular value and coinciding with the sixth connecting rod member section. The seventh connecting rod member section is a straight bar, and the fifth angle (having a fifth angular value) is formed by the seventh connecting rod member section and the eighth connecting rod member section. Moreover, the positive fifth angle is formed by the seventh connecting rod member section rotating counter-clockwise about the intersection of the seventh connecting rod member section and the eighth connecting rod member section by the fifth angular value and coinciding with the eighth connecting rod member section. The fourth angle is configured to be equal to the fifth angle. In embodiments, each of the fourth angle and the fifth angle is preferably in the range of 0-180°. In this embodiment, each of the fourth angle and the fifth angle is 90°. Further, in this Embodiment, the third angle is 0°, i.e. the fifth connecting rod member section is parallel to the seventh connecting rod member section, and the sixth connecting rod member section is parallel to the eighth connecting rod member section, with the fourth angle being equal to the fifth angle.

In this Embodiment, the intersection of the seventh connecting rod member 506 and the virtual connecting line between the axis of the first rotating shaft 520 and the second rotating shaft 521 is the remote center of motion D5. The first ration or the second ratio is also a ratio of the moving distance of the first (lower) end of the third connecting rod member 502 of the active components relative to the second rotating shaft 521 to the moving distance of the first (lower) end of the seventh connecting rod member 506 of the driven components relative to the remote center of motion D5 during the movement of the remote-center-of-motion mechanism 5.

With continued reference to FIG. 7, taking the second connecting rod member 501 as a reference line, the remote-center-of-motion mechanism 5 is able to rotate around the remote center of motion D5 when a driving torque is acted on the first connecting rod member 500 or the slide block device 510, and the remote-center-of-motion mechanisms 5 is able to make telescopic movement relative to the remote center of motion D5 when a driving torque is exerted on the fourth connecting rod member 503 or the sixth connecting rod member 505. Further, the remote-center-of-motion mechanism 5 is able to rotate around the remote center of motion D2 as well as to make telescopic movement relative to the remote center of motion D2 when one driving torque is acted on the first connecting rod member 500 or the slide block device 510 and another driving torque to the fourth connecting rod member 503 or the sixth connecting rod member 505. That is to say, the remote-center-of-motion mechanism 5 has two degrees of freedom of the rotational movement around remote center of motion D5 and the telescopic movement with respect to remote center of motion D5.

Embodiment 6

Figure 8:
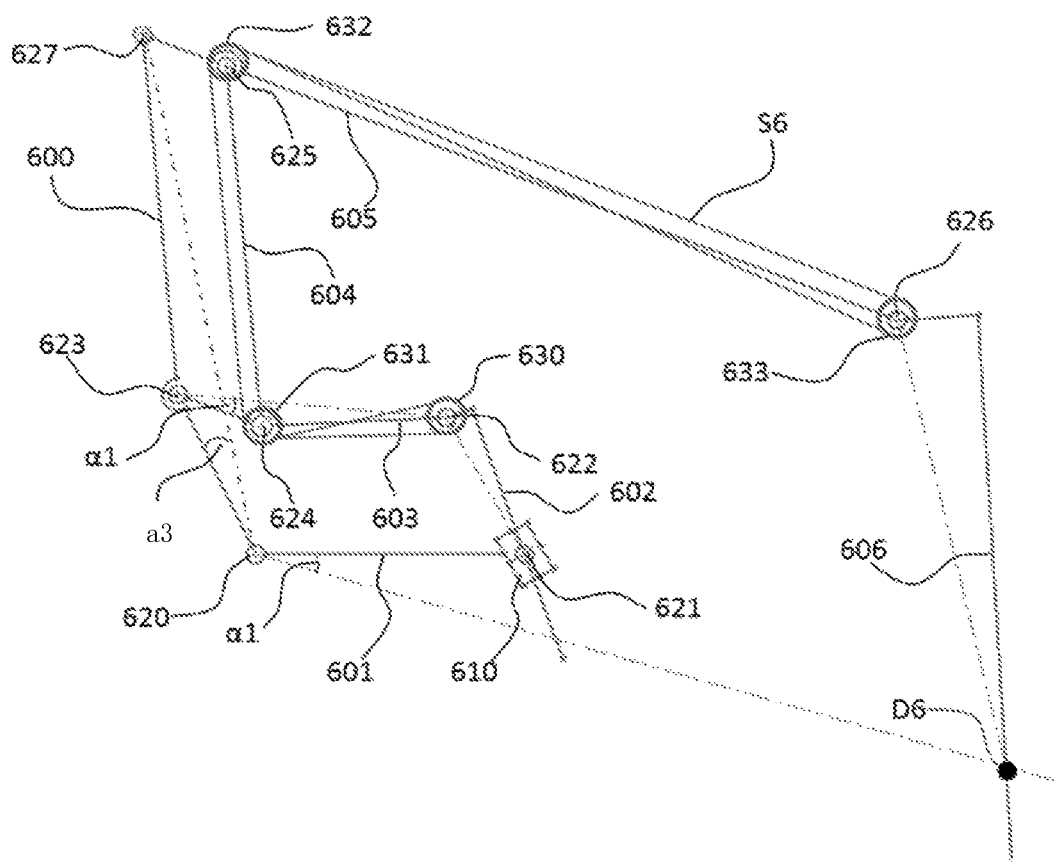
FIG. 8 is a schematic diagram illustrating the principle of a remote-center-of-motion mechanism according to Embodiment 6.

Reference is now made to FIG. 8, a schematic diagram illustrating the principle of a remote-center-of-motion mechanism according to Embodiment 6. As shown in FIG. 8, the remote-center-of-motion mechanism 6 includes active components, driven components and transmission components. Specifically, the active components include a first connecting rod member 600, a second connecting rod member 601, a third connecting rod member 602, a fourth connecting rod member 603 and a slide block device 610. A first (here, lower) end of the first connecting rod member 600 is rotatably connected to a first (here, proximal) end of the second connecting rod member 601 via a first rotating shaft 620. A second (here, distal) end of the second connecting rod member 601 is rotatably connected to the slide block device 610 via a second rotating shaft 621. The third connecting rod member 602 is slidably connected to the slide block device 610 and the third connecting rod member 602 passes through the axis of the second rotating shaft 621. A second (here, upper) end of the third connecting rod member 602 is rotatably connected to a second (here, distal) end of the fourth connecting rod member 603 via a third rotating shaft 622. A first (here, proximal) end of the fourth connecting rod member 603 is rotatably connected to the first connecting rod member 600 via a fourth rotating shaft 623. The third connecting rod member 602 passes through the axis of the second rotating shaft 621.

The driven components include a fifth connecting rod member 604, a sixth connecting rod member 605 and a seventh connecting rod member 606 connected in sequence. A second (here, upper) end of the fifth connecting rod member 604 is rotatably connected to the sixth connecting rod member 605 via a sixth rotating shaft 625. A second (here, distal) end of the sixth connecting rod member 605 is rotatably connected to a second (here, upper) end of the seventh connecting rod member 606 via a seventh rotating shaft 626. In addition, a first (here, lower) end of the fifth connecting rod member 604 is rotatably connected to the fourth connecting rod member 603 via a fifth rotating shaft 624, and a first (here, proximal) end of the sixth connecting rod member 605 is rotatably connected to a second (here, upper) end of the first connecting rod member 600 via an eighth rotating shaft 627.

The transmission components include a first runner 630, a second runner 631, a third runner 632, a fourth runner 633 and a flexible element S6. The first runner 630 and the third connecting rod member 602 rotate around the third rotating shaft 622 synchronously. The second runner 631 is sleeved over the fifth rotating shaft 624, and the third runner 632 is sleeved over the sixth rotating shaft 625. The fourth runner 633 and the seventh connecting rod member 306 rotate round the seventh rotating shaft 626 synchronously. The flexible element S6 is fixedly connected to each of the first runner 630 and the fourth runner 633 and is wound around and passes the second runner 631 and the third runner 632 through the sides of the second runner 631 and the third runner 632 away from the seventh connecting rod member, to form a closed transmission loop. The first runner 630 is equal to the fourth runner 633 in diameter, and the third runner 632 is equal to the second runner 631 in diameter.

That is, the winding path of the flexible element S6 can form angles similar to complementary wrap angles of a parallelogram. In other words, the flexible element S6 passes through the third runner 632 and the second runner 631 from sides of the third runner 632 and the second runner 631 away from the seventh connecting rod member 606, and forms a first wrap angle with the third runner 632 and a second wrap angle with the second runner 631. When a driving torque is acted on the first connecting rod member 600 or the slide block device 610, or when a driving torque is acted on the fourth connecting rod member 603 or the sixth connecting rod member 605, the change value of the first wrap angle equals to the change value of the second wrap angle in number.

In this Embodiment, a forward path and a return path of the flexible element S6 are formed at the same side of the third runner 632 and the second runner 631 away from the seventh connecting rod member. That is, the forward path and the return path of the flexible element S6 shares a same set of runners, i.e. the third runner 632 and the second runner 631, which are equal in diameter. In other embodiments, the forward path and the return path of the flexible element S6 may also use respective sets of runners. In this case, each of the third runner 632 and the second runner 631 comprises two runners forming two sets of runners. That is, the third runner 632 shown in FIG. 8 is replaced with a third runner A and a third runner B, and the second runner 631 shown in FIG. 8 is replaced with a second runner A and a second runner B. The third runner A and the second runner A constitute one set of runners, and the third runner B and the second runner B constitute the other set of runners. The forward path of the flexible element S6 may be constrained along one side of the third runner A and the second runner A away from the seventh connecting rod member, while the return path of the flexible element S6 may be constrained along one side of the third runner B and the second runner B away from the seventh connecting rod member. The third runner A is equal to the second runner A in diameter, and the third runner B is equal to the second runner B in diameter. The diameter of the third runner A and the diameter of the third runner B may be equal or not. The second runner 631 may be fixedly or rotatably connected to the fifth rotating shaft 624, i.e. relative motion is allowed between the second runner 631 and the fifth rotating shaft 624. The third runner 632 is connected to the sixth rotating shaft 625 in a similar manner.

In this Embodiment, the first runner 630 may be fixedly connected to the third connecting rod member 602 so as to achieve synchronous rotation of the first runner 630 and the third connecting rod member 602 about the third rotating shaft 622. Alternatively, each of the first runner 630 and the third connecting rod member 602 may be fixedly connected to the third rotating shaft 622 so that synchronous rotation of the first runner 630 and the third connecting rod member 602 about the third rotating shaft 622 is achieved.

A parallelogram can be formed by connecting virtual lines between the axis of the fourth rotating shaft 623, the axis of the fifth rotating shaft 624, the axis of the sixth rotating shaft 625 and the axis of the eighth rotating shaft 627.

The distance between the axis of the first rotating shaft 620 and the axis of the fourth rotating shaft 623 is in a first ratio to the distance between the axis of the first rotating shaft 620 and eighth rotating shaft 627, and the distance between the axis of the third rotating shaft 622 and the axis of the fourth rotating shaft 623 is in a second ratio to the distance between the axis of the eighth rotating shaft 627 and the axis of seventh rotating shaft 626. The first ratio is configured to be equal to the second ratio. Only when the first ratio is equal to the second ratio, can it be ensured that variation of the angle formed by the third connecting rod member 602 and the fourth connecting rod member 603 of the remote-center-of-motion mechanism 6 equals to the variation of the angle formed by the sixth connecting rod member 605 and the seventh connecting rod member 606 of the remote-center-of-motion mechanism 6 during the movement. In embodiments, each of the first ratio and the second ratio preferably ranges from 1/12 to 1/2. In this Embodiment, each of the first ratio and the second ratio is 1/6.

The first connecting line is formed by the virtual connecting line between the axis of the fifth rotating shaft 624 and the axis of the fourth rotating shaft 623, and the second connecting line is formed by the virtual connecting line between the axis of the fourth rotating shaft 623 and the axis of the third rotating shaft 622. The first angle a1 (having a first angular value) is formed by the first connecting line and the second connecting line. The second angle (having a second angular value) is formed by the third connecting rod member 602 and the seventh connecting rod member 606. The fourth connecting line is formed by the virtual connecting line between the axis of the first rotating shaft 620 and the axis of the fourth rotating shaft 623, and the fifth connecting line is formed by the virtual connecting line between the axis of the first rotating shaft 620 and the axis of the eighth rotating shaft 627. The third angle a3 (having a third angular value) is formed by the fourth connecting line and the fifth connecting line. The first angle a1, the second angle and the third angle a3 are configured to be equal.

Further, in embodiments, the sign of the first angle a1, the second angle and the third angle a3 is determined as follow: if the first connecting line coincides with the second connecting line after rotating counterclockwise about the axis of the fourth rotating shaft 623 by the first angular value, then the corresponding first angle a1 is positive; if the first connecting line coincides with the second connecting line after rotating clockwise about the axis of the fourth rotating shaft 623 by the first angular value, then the first corresponding angle is negative; and if the fourth connecting line coincides with the fifth connecting line after rotating clockwise or counterclockwise about the axis of the first rotating shaft 620 by the third angular value, then the corresponding third angle a3 is positive or negative, respectively.

In this Embodiment, each of the seventh connecting rod member 606 and the third connecting rod member 602 is a flexed rod. The third connecting rod member 602 includes a fifth connecting rod member section connected to the third rotating shaft 622 and a sixth connecting rod member section slidably connected to the slide block device 610, wherein the sixth connecting rod member section is a straight bar and passes through the axis of the second rotating shaft 621, and the fifth connecting rod member section is fixedly connected to the sixth connecting rod member section. The perpendicular segment between the axis of the third rotating shaft 622 and the sixth connecting rod member section defines a first segment. The seventh connecting rod member 606 includes a seventh connecting rod member section connected to the seventh rotating shaft 626 and an eighth connecting rod member section, wherein the eighth connecting rod member section is a straight bar and the seventh connecting rod member section is fixedly connected to the eighth connecting rod member section. The perpendicular segment between the axis of the seventh rotating shaft 626 and the eighth connecting rod member section defines a second segment. In this Embodiment, a length of the first segment is in a third ratio to a length of the second segment, and the third ratio is configured to be equal to the first ratio. That is, the third ratio preferably ranges from 1/12 to 1/2, more preferably is 1/6. Accordingly, the second angle is defined as: an angle formed by the second segment and a parallel line passing through the axis of the seventh rotating shaft 626 and paralleling to the first segment. Further, the sign of the second angle is determined as follow: if the parallel line coincides with the second segment after rotating clockwise or counterclockwise about the axis of the seventh rotating shaft 626 by the second angular value, then the corresponding second angle is positive or negative, respectively. The length and orientation of the second segment can decide the position and orientation of the axial line of the eighth connecting rod member section That is, the axial line of the eighth connecting rod member section is required to passing through one endpoint of the second segment as well as being perpendicular to the second segment in terms of the direction. The particular length of the eighth connecting rod member section is not limited thereto, and may be decided based on practical applications. In Embodiments, there is no specific limitation to the shape of each of the fifth connecting rod member section and the seventh connecting rod member section, which may be a straight bar, a curved rod, a flexed rod or a rod of other shape. In this Embodiment, there is also no specific limitation to the position of the connection between the seventh connecting rod member section and the eighth connecting rod member section.

In this embodiment, the fifth connecting rod member section is a straight bar, and the fourth angle (having a fourth angular value) is formed by the fifth connecting rod member section and the sixth connecting rod member section. Moreover, the sign of the fourth angle is determined as follow: the positive fourth angle is the angle formed by the fifth connecting rod member section rotating counterclockwise about the intersection of the fifth connecting rod member section and the sixth connecting rod member section by the fourth angular value and coinciding with the sixth connecting rod member section. The seventh connecting rod member section is also a straight bar, and the fifth angle (having a fifth angular value) is formed by the seventh connecting rod member section and the eighth connecting rod member section. Moreover, the sign of the fifth angle is determined as follow: the positive fifth angle is formed by the seventh connecting rod member section rotating counterclockwise about the intersection of the seventh connecting rod member section and the eighth connecting rod member section by the fifth angular value and coinciding with the eighth connecting rod member section. The fourth angle is configured to be equal to the fifth angle. In embodiments, each of the fourth angle and the fifth angle is in the range of 0-180°. In this embodiment, each of the fourth angle and the fifth angle is 90°.

According to the embodiments, a remote-center-of-motion mechanism can be achieved only when the first angle a1, the second angle and the third angle a3 are not only equal in absolute value but also are both positive or negative. It will be appreciated by those skilled in the art that, if an angle of a mechanism has a negative angular value whereas the its positive angular value being equivalent of the said negative angular value (i.e., 360° minus the absolute value of the angular value of an angle) equals to the angular values of the other two angles, then the said mechanism falls into the protection scope of the embodiments. Similarly, if an angle of a mechanism has a positive angular value whereas its negative angular value being equivalent of the its positive angular value (i.e., the absolute value of the angular value of an angle minus 360°) equals to the angular values of the other two angles, then the said mechanism falls into the protection scope of the embodiments.

In embodiments, the first angle, the second angle and the third angle preferably range from −30° to 30°. In this embodiment, each of the first angle a1, the second angle and the third angle a3 is positive, particularly 15°, i.e. the fourth connecting rod member 603 being a flexed rod as shown in FIG. 8. Specifically, the fourth connecting rod member 603 includes a first connecting rod member section between the fourth rotating shaft 623 and the fifth rotating shaft 624, and a second connecting rod member section between the third rotating shaft 622 and the fifth rotating shaft 624, wherein the first connecting rod member section is fixedly connected to the second connecting rod member section with a flexed angle. More preferably, each of the first connecting rod member section and the second connecting rod member section is a straight bar, and the fifth rotating shaft 624 is situated below a virtual connecting line between the axis of the third rotating shaft 622 and the axis of the fourth rotating shaft 623 (i.e., the first angle a1 is formed by the first connecting line rotating counterclockwise about the axis of the fifth rotating shaft 624 by the first angular value and then coinciding with the second connecting line). Similarly, the first connecting rod member 600 is also a flexed rod. Specifically, the first connecting rod member 600 includes a third connecting rod member section between the first rotating shaft 620 and the fourth rotating shaft 623 and a fourth connecting rod member section between the fourth rotating shaft 623 and the eighth rotating shaft 627, wherein the third connecting rod member section is fixedly connected to the fourth connecting rod member section with a flexed angle. More preferably, each of the third connecting rod member section and the fourth connecting rod member section is a straight bar, and the fourth rotating shaft 623 is situated at the left side of the virtual connecting line between the axis of the first rotating shaft 620 and the axis of the eighth rotating shaft 627 (i.e., the third angle a3 is formed by the fourth connecting line rotating clockwise about the axis of the fourth rotating shaft 623 by the third angular value and then coinciding with the fifth connecting line).

As such, the sixth connecting line, formed by the virtual connecting line between the axis of the first rotating shaft 620 and the axis of the second rotating shaft 621, rotates clockwise about the axis of the first rotating shaft 620 by the first angle a1, and then intersects with the seventh connecting rod member 606, wherein the intersection is the remote center of motion D6. Likewise, the first ratio or the second ratio is equal to the ratio of the moving distance of the first (lower) end of the third connecting rod member 602 of the active components relative to the second rotating shaft 621 to the moving distance of the first (lower) end of the seventh connecting rod member 606 of the driven components relative to the remote center of motion D6 during the movement of the remote-center-of-motion mechanism 6.

Similarly, when the first angle, the second angle and the third angle are all negative, the sixth connecting line rotates counterclockwise about the axis of the first rotating shaft 620 by the first angle a1, and then intersects with the seventh connecting rod member 606, wherein the intersection is the remote center of motion D6.

With continued reference to FIG. 8, taking the second connecting rod member 601 as a reference line, the remote-center-of-motion mechanism 6 is able to rotate around the remote center of motion D6 when a driving torque is acted on the first connecting rod member 600 or the slide block device 610, and the remote-center-of-motion mechanism 6 is able to make telescopic movement relative to the remote center of motion D6 when a driving torque is exerted on the fourth connecting rod member 603 or the sixth connecting rod member 605. Further, the remote-center-of-motion mechanism 6 is able to rotate around the remote center of motion D6 as well as to make telescopic movement relative to the remote center of motion D6 when one driving torque is acted on the first connecting rod member 600 or the slide block device 610 and another driving torque is applied to the fourth connecting rod member 603 or the sixth connecting rod member 605. That is to say, the remote-center-of-motion mechanism 6 has two degrees of freedom of the rotational movement around remote center of motion D6 and the telescopic movement with respect to remote center of motion D6.

Embodiment 7

Some variations of the above embodiments are also within the protection scope of the embodiments. For example, in the above embodiments, the second end of the second connecting rod member is rotatably connected to the slide block device via the second rotating shaft, and the third connecting rod member is slidably connected to the slide block device and passes through the pivot point of the second rotating shaft.

Figure 9:
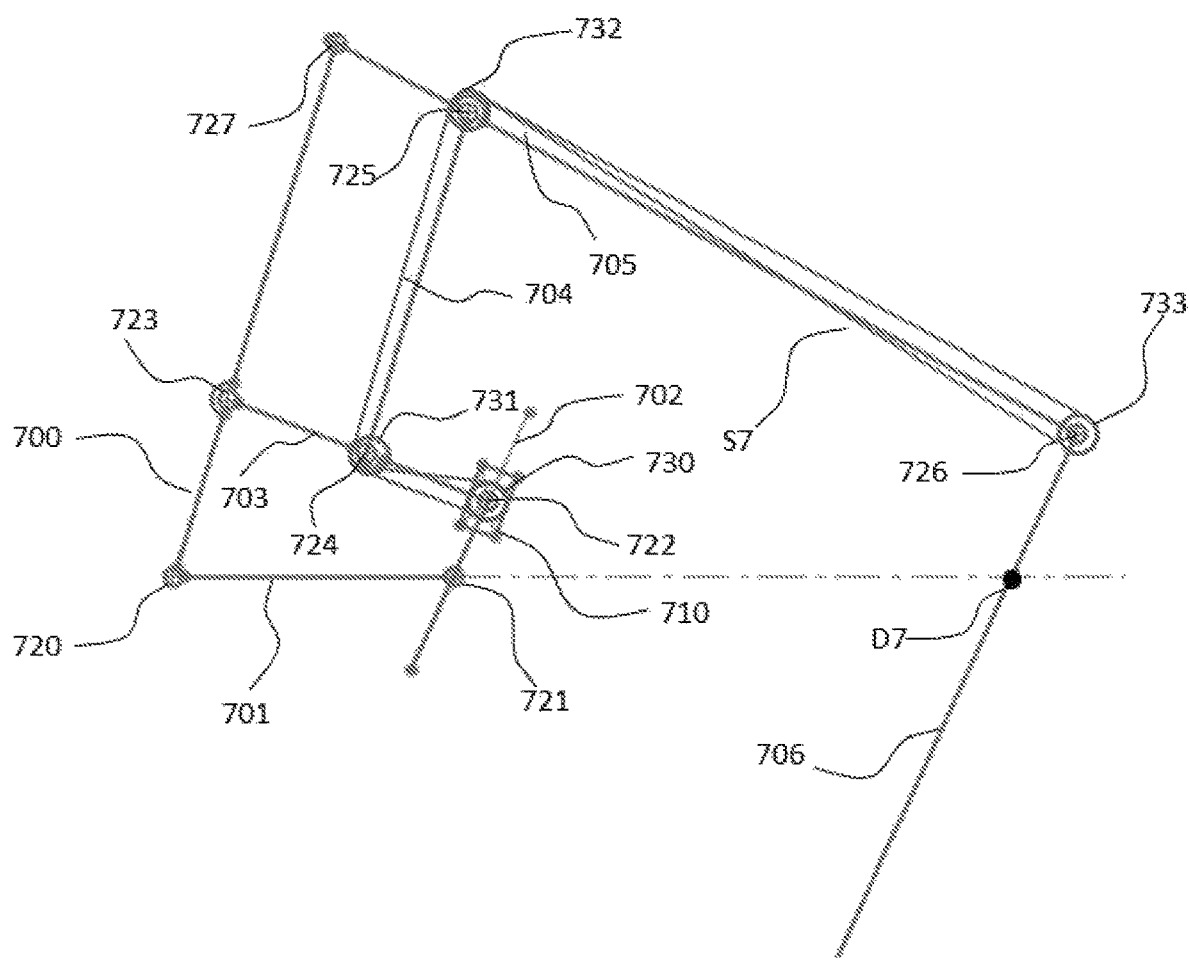
FIG. 9 is a schematic diagram illustrating the principles of a remote-center-of-motion mechanism according to Embodiment 7.

Differing from Embodiments 1 to 4, in Embodiment 7 shown in FIG. 9, the second end of the second connecting rod member 701 is rotatably connected to the third connecting rod member 702 via the second rotating shaft 721, the second end of the fourth connecting rod member 703 being rotatably connected to the slide block device 710 via the third rotating shaft 722, the third connecting rod member 702 being slidably connected to the slide block device 710 and passes through the axis of the third rotating shaft 722, the slide block device 710 and the first runner 730 rotating about the third rotating shaft 722 synchronously. In this Embodiment, the second angle is defined as: the second angle is formed by the third connecting line, which is formed by a virtual connecting line between the axis of the second rotating shaft 721 and the axis of third rotating shaft 722, and the seventh connecting rod member 706. The sign of the second angle is determined as follow: assuming that the first parallel line is a virtual straight ling paralleling to the axial line of the seventh connecting rod member 706 and passing the axis of the second rotating shaft 721, if the third connecting line coincides with the first parallel line after rotating clockwise or counterclockwise about the axis of the second rotating shaft 721 by the second angular value, then the corresponding second angle is positive or negative, respectively. Further, in this Embodiment, the first angle, the second angle and the third angle are all 0°.

Embodiment 8

Figure 10:
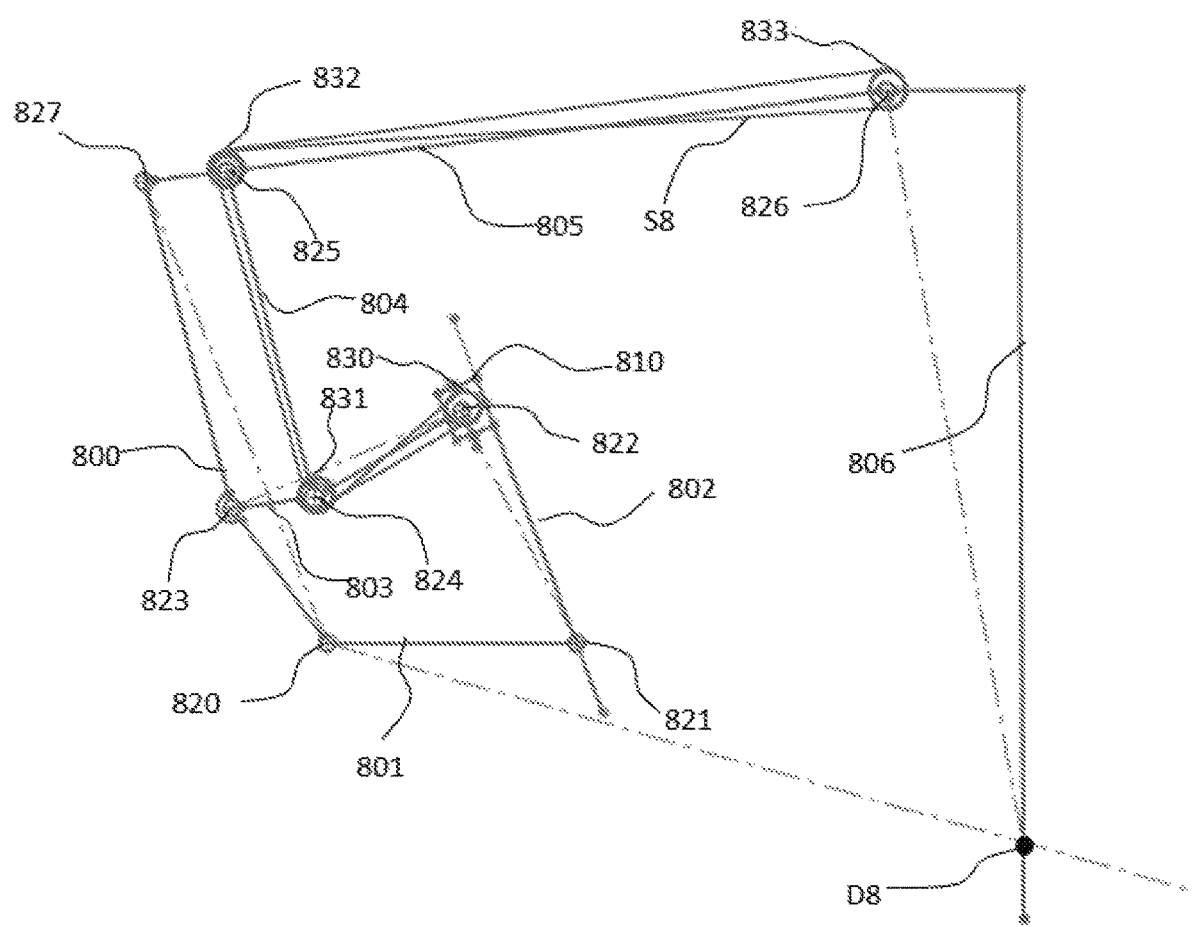
FIG. 10 is a schematic diagram illustrating the principles of a remote-center-of-motion mechanism according to Embodiment 8.

Differing from Embodiments 5 to 6, in Embodiment 8 shown in FIG. 10, the second end of the second connecting rod member 801 is rotatably connected to the third connecting rod member 802 via the second rotating shaft 821, the second end of the fourth connecting rod member 803 being rotatably connected to the slide block device 810 via the third rotating shaft 822, the third connecting rod member 802 being a straight bar and slidably connected to the slide block device 810, the third connecting rod member 802 does not passing through the pivot point of the third rotating shaft 822. In this embodiment, a perpendicular segment between the third rotating shaft 822 and the third connecting rod member 802 defines a first segment, and a perpendicular segment between the seventh rotating shaft 826 and the seventh connecting rod member 806 defines a second segment. A second angle is formed by the third connecting rod member 802 and the seventh connecting rod member 806. Further, the second angle is defined as an angle formed by the second segment and the parallel line passing through the axis of the seventh rotating shaft 826 and paralleling to the first segment. The sign of the second angle is determined as follow: if the parallel line coincides with the second segment after rotating clockwise or counterclockwise about the axis of the seventh rotating shaft 826 by the second angular value, then the corresponding second angle is positive or negative, respectively.

The above description is only a description of the preferred embodiments of the present application, and is not intended to limit the scope of the present application. Any changes and modifications made by those skilled in the art according to the above disclosure are all fall within the protection scope of the appended claims.

What is claimed is:

1. A remote-center-of-motion mechanism comprising active components, driven components and transmission components, wherein:

the active components comprise a first connecting rod member, a second connecting rod member, a third connecting rod member, a fourth connecting rod member and a slide block device, the first connecting rod member having a first end rotatably connected to a first end of the second connecting rod member via a first rotating shaft, the second connecting rod member having a second end rotatably connected to the slide block device via a second rotating shaft, the third connecting rod member being slidably connected to the slide block device, the third connecting rod member passing through an axis of the second rotating shaft, the third connecting rod member having a second end rotatably connected to a second end of the fourth connecting rod member via a third rotating shaft, the fourth connecting rod member having a first end rotatably connected to the first connecting rod member via a fourth rotating shaft;

the driven components comprise a fifth connecting rod member, a sixth connecting rod member and a seventh connecting rod member connected in sequence, the fifth connecting rod member having a first end rotatably connected to the fourth connecting rod member via a fifth rotating shaft, the fifth connecting rod member having a second end rotatably connected to the sixth connecting rod member via a sixth rotating shaft, the sixth connecting rod member having a second end rotatably connected to a second end of the seventh connecting rod member via a seventh rotating shaft, the sixth connecting rod member having a first end rotatably connected to a second end of the first connecting rod member via an eighth rotating shaft;

the transmission components comprise a first runner, a second runner, a third runner, a fourth runner and a flexible element, wherein:

the first runner and the third connecting rod member rotate about the third rotating shaft synchronously, the fourth runner and the seventh connecting rod member rotate about the seventh rotating shaft synchronously, and the first runner equals to the fourth runner in diameter, wherein the second runner is sleeved over the fifth rotating shaft, the third runner is sleeved over the sixth rotating shaft, the second runner equals to the third runner in diameter, the flexible element is fixedly connected to each of the first runner and the fourth runner and is wound around and passes the second runner and the third runner through sides of the second runner and the third runner away from the seventh connecting rod member, to form a closed transmission loop;

or wherein the first runner and the third connecting rod member rotate about the third rotating shaft synchronously, the fourth runner and the seventh connecting rod member rotate about the seventh rotating shaft synchronously, and the first runner equals to the fourth runner in diameter, and wherein the second runner is sleeved over the fourth rotating shaft, the third runner is sleeved over the eighth rotating shaft, the second runner equals to the third runner in diameter, the flexible element is fixedly connected to each of the first runner and the fourth runner and is wound around and passes the second runner and the third runner through sides of the second runner and the third runner away from the seventh connecting rod member, to form a closed transmission loop;

wherein a parallelogram can be formed by connecting virtual lines between an axis of the fourth rotating shaft, an axis of the fifth rotating shaft, an axis of the sixth rotating shaft and an axis of the eighth rotating shaft;

wherein each of the third connecting rod member and the seventh connecting rod members is a straight bar;

wherein a distance between an axis of the first rotating shaft and the axis of the fourth rotating shaft is in a first ratio to a distance between the axis of the first rotating shaft and the axis of the eighth rotating shaft, and a distance between an axis of the third rotating shaft and the axis of the fourth rotating shaft is in a second ratio to a distance between the axis of the eighth rotating shaft and an axis of the seventh rotating shaft, wherein the first ratio and the second ratio are configured to be equal; and wherein a first connecting line is formed by a virtual connecting line between the axis of the fifth rotating shaft and the axis of the fourth rotating shaft, a second connecting line is formed by a virtual connecting line between the axis of the fourth rotating shaft and the axis of the third rotating shaft, and a first angle is formed by the first connecting line and the second connecting line; wherein a third connecting line is formed by a virtual connecting line between the axis of the second rotating shaft and the axis of the third rotating shaft, and a second angle is formed by the third connecting line and the seventh connecting rod member; wherein a fourth connecting line is formed by a virtual connecting line between the axis of the first rotating shaft and the axis of the fourth rotating shaft, a fifth connecting line is formed by a virtual connecting line between the axis of the first rotating shaft and the axis of the eighth rotating shaft, and a third angle is formed by the fourth connecting line and the fifth connecting line; wherein the first angle, the second angle and the third angle are configured to be equal.

2. The remote-center-of-motion mechanism according to claim 1, wherein the first angle ranges from −30° to 30°.

3. The remote-center-of-motion mechanism according to claim 2, wherein the first angle is 0°, −15° or 15°.

4. The remote-center-of-motion mechanism according to claim 1, wherein the first ratio ranges from 1/12 to 1/2.

5. The remote-center-of-motion mechanism according to claim 1, wherein each of the second runner and the third runner is a single wheel, or each of the second runner and the third runner is implemented as a set of single wheels.

6. A remote-center-of-motion mechanism comprising active components, driven components and transmission components, wherein:

the active components comprise a first connecting rod member, a second connecting rod member, a third connecting rod member, a fourth connecting rod member and a slide block device, the first connecting rod member having a first end rotatably connected to a first end of the second connecting rod member via a first rotating shaft, the second connecting rod member having a second end rotatably connected to the slide block device via a second rotating shaft, the third connecting rod member being slidably connected to the slide block device, the third connecting rod member passing through an axis of the second rotating shaft, the third connecting rod member having a second end rotatably connected to a second end of the fourth connecting rod member via a third rotating shaft, the fourth connecting rod member having a first end rotatably connected to the first connecting rod member via a fourth rotating shaft;

the driven components comprise a fifth connecting rod member, a sixth connecting rod member and a seventh connecting rod member connected in sequence, the fifth connecting rod member having a first end rotatably connected to the fourth connecting rod member via a fifth rotating shaft, the fifth connecting rod member having a second end rotatably connected to the sixth connecting rod member via a sixth rotating shaft, the sixth connecting rod member having a second end rotatably connected to a second end of the seventh connecting rod member via a seventh rotating shaft, the sixth connecting rod member having a first end rotatably connected to a second end of the first connecting rod member via an eighth rotating shaft;

the transmission components comprise a first runner, a second runner, a third runner, a fourth runner and a flexible element, wherein:

the first runner and the third connecting rod member rotate about the third rotating shaft synchronously, the fourth runner and the seventh connecting rod member rotate about the seventh rotating shaft synchronously, the first runner equals to the fourth runner in diameter, the second runner is sleeved over the fifth rotating shaft, the third runner is sleeved over the sixth rotating shaft, the second runner equals to the third runner in diameter, the flexible element is fixedly connected to each of the first runner and the fourth runner and is wound around and passes the second runner and the third runner through sides of the second runner and the third runner away from the seventh connecting rod member, to form a closed transmission loop;

or wherein the first runner and the third connecting rod member rotate about the third rotating shaft synchronously, the fourth runner and the seventh connecting rod member rotate about the seventh rotating shaft synchronously, the first runner equals to the fourth runner in diameter, and wherein the second runner is sleeved over the fourth rotating shaft, the third runner is sleeved over the eighth rotating shaft, the second runner equals to the third runner in diameter, the flexible element is fixedly connected to each of the first runner and the fourth runner and is wound around and passes the second runner and the third runner through sides of the second runner and the third runner away from the seventh connecting rod member, to form a closed transmission loop;

wherein a parallelogram can be formed by connecting virtual lines between an axis of the fourth rotating shaft, an axis of the fifth rotating shaft, an axis of the sixth rotating shaft and an axis of the eighth rotating shaft;

wherein the third connecting rod member comprises a fifth connecting rod member section connected to the third rotating shaft and a sixth connecting rod member section slidably connected to the slide block device, the sixth connecting rod member section is a straight bar, the fifth connecting rod member section is fixedly connected to the sixth connecting rod member section, and a distance from the third rotating shaft to the sixth connecting rod member section defines a first segment; wherein the seventh connecting rod member comprises a seventh connecting rod member section connected to the seventh rotating shaft and an eighth connecting rod member section, the eighth connecting rod member section is a straight bar, the seventh connecting rod member section is fixedly connected to the eighth connecting rod member section, and a distance from the seventh rotating shaft to the eighth connecting rod member section defines a second segment;

wherein a distance between an axis of the first rotating shaft and the axis of the fourth rotating shaft is in a first ratio to a distance between the axis of the first rotating shaft and the axis of the eighth rotating shaft, a distance between an axis of the third rotating shaft and the axis of the fourth rotating shaft is in a second ratio to a distance between the axis of the eighth rotating shaft and an axis of seventh rotating shaft, the first segment is in a third ratio to the second segment, and the first ratio, the second ratio and the third ratio are configured to be equal; and wherein a first connecting line is formed by a virtual connecting line between the axis of the fifth rotating shaft and the axis of the fourth rotating shaft, a second connecting line is formed by a virtual connecting line between the axis of the fourth rotating shaft and the axis of the third rotating shaft, a first angle is formed by the first connecting line and the second connecting line and a second angle is formed between the third connecting rod member and the seventh connecting rod member; wherein a fourth connecting line is formed by a virtual connecting line between the axis of the first rotating shaft and the axis of the fourth rotating shaft, a fifth connecting line is formed by a virtual connecting line between the axis of the first rotating shaft and the axis of the eighth rotating shaft, and a third angle is formed by the fourth connecting line and the fifth connecting line; wherein the first angle, the second angle and the third angle are configured to be equal.

7. The remote-center-of-motion mechanism according to claim 6, wherein the first angle ranges from −30° to 30°.

8. The remote-center-of-motion mechanism according to claim 7, wherein the first angle is 0°, −15° or 15°.

9. The remote-center-of-motion mechanism according to claim 6, wherein the first ratio ranges from 1/12 to 1/2.

10. The remote-center-of-motion mechanism according to claim 6, wherein the fifth connecting rod member section is a straight bar with a fourth angle being formed by the fifth connecting rod member section and the sixth connecting rod member section, and the seventh connecting rod member section is also a straight bar with a fifth angle being formed by the seventh connecting rod member section and the eighth connecting rod member section, wherein the fifth angle is configured to be equal to the fourth angle.

11. The remote-center-of-motion mechanism according to claim 6, wherein the fourth angle ranges from 0° to 180°.

12. A remote-center-of-motion mechanism comprising active components, driven components and transmission components, wherein:

the active components comprise a first connecting rod member, a second connecting rod member, a third connecting rod member, a fourth connecting rod member and a slide block device, the first connecting rod member having a first end rotatably connected to a first end of the second connecting rod member via a first rotating shaft, the second connecting rod member having a second end rotatably connected to the third connecting rod member via a second rotating shaft, the fourth connecting rod member having a second end rotatably connected to the slide block device via a third rotating shaft, the third connecting rod member being slidably connected to the slide block device, the third connecting rod member passing through an axis of the third rotating shaft, the fourth connecting rod member having a first end rotatably connected to the first connecting rod member via a fourth rotating shaft;

the driven components comprise a fifth connecting rod member, a sixth connecting rod member and a seventh connecting rod member connected in sequence, the fifth connecting rod member having a first end rotatably connected to the fourth connecting rod member via a fifth rotating shaft, the fifth connecting rod member having a second end rotatably connected to the sixth connecting rod member via a sixth rotating shaft, the sixth connecting rod member having a second end rotatably connected to a second end of the seventh connecting rod member via a seventh rotating shaft, the sixth connecting rod member having a first end rotatably connected to a second end of the first connecting rod member via an eighth rotating shaft;

the transmission components comprise a first runner, a second runner, a third runner, a fourth runner and a flexible element, wherein:

the first runner and the third connecting rod member rotate about the third rotating shaft synchronously, the fourth runner and the seventh connecting rod member rotate about the seventh rotating shaft synchronously, the first runner equals to the fourth runner in diameter, wherein the second runner is sleeved over the fifth rotating shaft, the third runner is sleeved over the sixth rotating shaft, the second runner equals to the third runner in diameter, the flexible element is fixedly connected to each of the first runner and the fourth runner and is wound around and passes the second runner and the third runner through sides of the second runner and the third runner away from the seventh connecting rod member, to form a closed transmission loop;

or wherein the first runner and the third connecting rod member rotate about the third rotating shaft synchronously, the fourth runner and the seventh connecting rod member rotate about the seventh rotating shaft synchronously, the first runner equals to the fourth runner in diameter, and wherein the second runner is sleeved over the fourth rotating shaft, the third runner is sleeved over the eighth rotating shaft, the second runner equals to the third runner in diameter, the flexible element is fixedly connected to each of the first runner and the fourth runner and is wound around and passes the second runner and the third runner through sides of the second runner and the third runner away from the seventh connecting rod member, to form a closed transmission loop;

wherein a parallelogram can be formed by connecting virtual lines between an axis of the fourth rotating shaft, an axis of the fifth rotating shaft, an axis of the sixth rotating shaft and an axis of the eighth rotating shaft;

wherein each of the third connecting rod member and the seventh connecting rod members is a straight bar;

wherein a distance between an axis of the first rotating shaft and the axis of the fourth rotating shaft is in a first ratio to a distance between the axis of the first rotating shaft and the axis of the eighth rotating shaft, and a distance between the axis of the third rotating shaft and the axis of the fourth rotating shaft is in a second ratio to a distance between the axis of the eighth rotating shaft and an axis of the seventh rotating shaft, wherein the first ratio is configured to be equal to the second ratio; and wherein a first connecting line is formed by a virtual connecting line between the axis of the fifth rotating shaft and the axis of the fourth rotating shaft, a second connecting line is formed by a virtual connecting line between the axis of the fourth rotating shaft and the axis of the third rotating shaft, and a first angle is formed by the first connecting line and the second connecting line; wherein a third connecting line is formed by a virtual connecting line between an axis of the second rotating shaft and the axis of third rotating shaft, and a second angle is formed by the third connecting line and the seventh connecting rod member; wherein a fourth connecting line is formed by a virtual connecting line between the axis of the first rotating shaft and the axis of the fourth rotating shaft, a fifth connecting line is formed by a virtual connecting line between the axis of the first rotating shaft and the axis of the eighth rotating shaft, and a third angle is formed by the fourth connecting line and the fifth connecting line; wherein the first angle, the second angle and the third angle are configured to be equal.

13. A remote-center-of-motion mechanism comprising active components, driven components and transmission components, wherein:

the active components comprise a first connecting rod member, a second connecting rod member, a third connecting rod member, a fourth connecting rod member and a slide block device, the first connecting rod member having a first end rotatably connected to a first end of the second connecting rod member via a first rotating shaft, the second connecting rod member having a second end rotatably connected to the third connecting rod member via a second rotating shaft, the fourth connecting rod member having a second end rotatably connected to the slide block device via a third rotating shaft, the third connecting rod member being slidably connected to the slide block device and not passing through an axis of the third rotating shaft, the fourth connecting rod member having a first end rotatably connected to the first connecting rod member via a fourth rotating shaft;

the driven components comprise a fifth connecting rod member, a sixth connecting rod member and a seventh connecting rod member connected in sequence, the fifth connecting rod member having a first end rotatably connected to the fourth connecting rod member via a fifth rotating shaft, the fifth connecting rod member having a second end rotatably connected to the sixth connecting rod member via a sixth rotating shaft, the sixth connecting rod member having a second end rotatably connected to a second end of the seventh connecting rod member via a seventh rotating shaft, the sixth connecting rod member having a first end rotatably connected to a second end of the first connecting rod member via an eighth rotating shaft;

the transmission components comprise a first runner, a second runner, a third runner, a fourth runner and a flexible element, wherein:

the first runner and the third connecting rod member rotate about the third rotating shaft synchronously, the fourth runner and the seventh connecting rod member rotate about the seventh rotating shaft synchronously, and the first runner equals to the fourth runner in diameter, and wherein the second runner is sleeved over the fifth rotating shaft, the third runner is sleeved over the sixth rotating shaft, the second runner equals to the third runner in diameter, the flexible element is fixedly connected to each of the first runner and the fourth runner and is wound around and passes the second runner and the third runner through sides of the second runner and the third runner away from the seventh connecting rod member, to form a closed transmission loop;

or wherein the first runner and the third connecting rod member rotate about the third rotating shaft synchronously, the fourth runner and the seventh connecting rod member rotate about the seventh rotating shaft synchronously, and the first runner equals to the fourth runner in diameter, and wherein the second runner is sleeved over the fourth rotating shaft, the third runner is sleeved over the eighth rotating shaft, the second runner equals to the third runner in diameter, the flexible element is fixedly connected to each of the first runner and the fourth runner and is wound around and passes the second runner and the third runner through sides of the second runner and the third runner away from the seventh connecting rod member, to form a closed transmission loop;

wherein a parallelogram can be formed by connecting virtual lines between an axis of the fourth rotating shaft, an axis of the fifth rotating shaft, an axis of the sixth rotating shaft and an axis of the eighth rotating shaft;

wherein the third connecting rod member is a straight bar, a distance from the third rotating shaft to the third connecting rod member defines a first segment; wherein the seventh connecting rod member comprises a seventh connecting rod member section connected to the seventh rotating shaft and an eighth connecting rod member section, and the seventh connecting rod member section is partially fixedly connected to the eighth connecting rod member section; wherein the eighth connecting rod member section is a straight bar, and a distance from the seventh rotating shaft to the eighth connecting rod member section defines a second segment;

wherein a distance between an axis of the first rotating shaft and the axis of the fourth rotating shaft is in a first ratio to a distance between the axis of the first rotating shaft and the axis of the eighth rotating shaft, a distance between an axis of the third rotating shaft and the axis of the fourth rotating shaft is in a second ratio to a distance between the axis of the eighth rotating shaft and an axis of the seventh rotating shaft, the first segment is in a third ratio to the second segment, and the first ratio, the second ratio and the third ratio are configured to be equal; and wherein a first connecting line is formed by a virtual connecting line between the axis of the fifth rotating shaft and the axis of the fourth rotating shaft, a second connecting line is formed by a virtual connecting line between the axis of the fourth rotating shaft and the axis of the third rotating shaft, a first angle is formed by the first connecting line and the second connecting line, and a second angle is formed by the third connecting rod member and the seventh connecting rod member, wherein a fourth connecting line is formed by a virtual connecting line between the axis of the first rotating shaft and the axis of the fourth rotating shaft, a fifth connecting line is formed by a virtual connecting line between the axis of the first rotating shaft and the axis of the eighth rotating shaft, a third angle is formed by the fourth connecting line and the fifth connecting line, and the first angle, the second angle and the third angle are configured to be equal.

* * * * *